US008845927B2

(12) United States Patent
Breen et al.

(10) Patent No.: US 8,845,927 B2
(45) Date of Patent: Sep. 30, 2014

(54) FUNCTIONALIZED NANOPARTICLES AND METHOD

(75) Inventors: Craig Breen, Somerville, MA (US); Marshall Cox, North Haven, CT (US); Jonathan S. Steckel, Bedford, MA (US)

(73) Assignee: QD Vision, Inc., Lexington, MA (US)

( * ) Notice: Subject to any disclaimer, the term of this patent is extended or adjusted under 35 U.S.C. 154(b) by 0 days.

(21) Appl. No.: 12/722,028

(22) Filed: Mar. 11, 2010

(65) Prior Publication Data
US 2010/0283014 A1 Nov. 11, 2010

Related U.S. Application Data

(63) Continuation of application No. PCT/US2008/010651, filed on Sep. 12, 2008, and a continuation-in-part of application No. PCT/US2008/024750, filed on Dec. 3, 2007, and a continuation-in-part of application No. PCT/US2008/007902, filed on Jun. 25, 2008, and a continuation-in-part of application No. PCT/US2007/013152, filed on Jun. 4, 2007.

(60) Provisional application No. 60/971,887, filed on Sep. 12, 2007, provisional application No. 61/083,998, filed on Jul. 28, 2008, provisional application No. 60/971,885, filed on Sep. 12, 2007, provisional application No. 60/992,598, filed on Dec. 5, 2007, provisional application No. 60/973,644, filed on Sep. 19, 2007, provisional application No. 61/016,227, filed on Dec. 21, 2007, provisional application No. 60/810,767, filed on Jun. 2, 2006, provisional application No. 60/810,914, filed on Jun. 5, 2006, provisional application No. 60/804,921, filed on Jun. 15, 2006, provisional application No. 60/825,373, filed on Sep. 12, 2006, provisional application No. 60/825,374, filed on Sep. 12, 2006, provisional application No. 60/825,370, filed on Sep. 12, 2006, provisional application No. 60/886,261, filed on Jan. 23, 2007.

(51) Int. Cl.
C09K 11/70 (2006.01)
C30B 29/60 (2006.01)
C09K 11/88 (2006.01)
C09K 11/56 (2006.01)
G01N 33/58 (2006.01)
C30B 33/00 (2006.01)
G01N 33/543 (2006.01)
B82Y 30/00 (2011.01)

(52) U.S. Cl.
CPC ............ C09K 11/883 (2013.01); C30B 29/605 (2013.01); C09K 11/881 (2013.01); C09K 11/565 (2013.01); G01N 33/587 (2013.01); C30B 33/00 (2013.01); G01N 33/54346 (2013.01); B82Y 30/00 (2013.01)

USPC ........... 252/301.4 P; 252/519.2; 252/301.6 S; 252/301.6 P; 252/301.4 S; 257/103

(58) Field of Classification Search
USPC ............ 252/519.2, 301.6 S, 301.6 P, 301.4 S, 252/301.4 P; 257/103
See application file for complete search history.

(56) References Cited

U.S. PATENT DOCUMENTS

| | | |
|---|---|---|
| 4,789,753 A | 12/1988 | Billig et al. |
| 4,994,429 A | 2/1991 | Wieserman et al. |
| 5,064,718 A | 11/1991 | Buscall et al. |
| 5,399,694 A | 3/1995 | Riess et al. |
| 5,648,362 A | 7/1997 | Riess et al. |
| 5,677,545 A * | 10/1997 | Shi et al. .......................... 257/40 |
| 5,751,018 A | 5/1998 | Alivisatos et al. |
| 5,981,467 A | 11/1999 | Hogan, Jr. |
| 6,114,038 A | 9/2000 | Castro et al. |
| 6,207,229 B1 | 3/2001 | Bawendi et al. |
| 6,235,540 B1 | 5/2001 | Siiman et al. |
| 6,251,303 B1 | 6/2001 | Bawendi et al. |
| 6,306,610 B1 | 10/2001 | Bawendi et al. |
| 6,319,426 B1 * | 11/2001 | Bawendi et al. ........ 252/301.4 R |
| 6,319,607 B1 | 11/2001 | Barbera-Guillium et al. |
| 6,322,901 B1 | 11/2001 | Bawendi et al. |
| 6,444,143 B2 | 9/2002 | Bawendi et al. |

(Continued)

FOREIGN PATENT DOCUMENTS

AU A-54514/96 12/1995
EP 0745646 A1 12/1996

(Continued)

OTHER PUBLICATIONS

CAS reg. No. 57877-93-7, Nov. 16, 1984.*
Coe-Sullivan, et al., Adv. Func. Mater., 2005, 15, 1117-1124.
Dabbousi, et al., J. Phys. Chem. B, 1997, 101, 9463.
Diamente, et al., Langmuir, 2006, 22, 1782-1788.
Doussineau, et al., Synlett 2004, No. 10, 1735-1738.
European Counterpart EP Application No. 08 831 106.3-1223—Extended European Search Report dated Jan. 13, 2011.

(Continued)

Primary Examiner — Douglas McGinty

(57) ABSTRACT

A nanoparticle has a semiconductor nanocrystal capable of emitting light. The nanoparticle further includes a ligand attached to a surface of the coating. The ligand is represented by the formula: X-Sp-Z, wherein X represents, e.g., a primary amine group, a secondary amine group, a urea, a thiourea, an imidizole group, an amide group, a phosphonic or arsonic acid group, a phosphinic or arsinic acid group, a phosphate or arsenate group, a phosphine or arsine oxide group; Sp represents a spacer group, such as a group capable of allowing a transfer of charge or an insulating group; and Z represents: (i) reactive group capable of communicating specific chemical properties to the nanocrystal as well as provide specific chemical reactivity to the surface of the nanocrystal, and/or (ii) a group that is cyclic, halogenated, or polar a-protic.

23 Claims, 4 Drawing Sheets

(56) References Cited

U.S. PATENT DOCUMENTS

| | | | |
|---|---|---|---|
| 6,468,808 B1 | 10/2002 | Nie et al. | |
| 6,473,554 B1 | 10/2002 | Pelka et al. | |
| 6,548,168 B1 | 4/2003 | Mulvaney et al. | |
| 6,563,186 B2 | 5/2003 | Liu et al. | |
| 6,714,711 B1 | 3/2004 | Lieberman et al. | |
| 6,797,412 B1 | 9/2004 | Jain et al. | |
| 6,801,270 B2 | 10/2004 | Faris et al. | |
| 6,805,922 B2 | 10/2004 | Heeney et al. | |
| 6,855,202 B2 | 2/2005 | Alivisatos et al. | |
| 6,869,545 B2* | 3/2005 | Peng et al. | 252/301.6 S |
| 6,887,517 B1 | 5/2005 | Cook et al. | |
| 6,949,206 B2* | 9/2005 | Whiteford et al. | 252/500 |
| 7,041,362 B2 | 5/2006 | Barbera-Guillem | |
| 7,065,285 B2 | 6/2006 | Chen et al. | |
| 7,108,915 B2 | 9/2006 | Adams et al. | |
| 7,147,917 B2 | 12/2006 | Adams et al. | |
| 7,160,613 B2* | 1/2007 | Bawendi et al. | 428/403 |
| 7,190,870 B2 | 3/2007 | Sundar et al. | |
| 7,198,847 B2 | 4/2007 | Naasani | |
| 7,199,393 B2 | 4/2007 | Park et al. | |
| 7,214,428 B2 | 5/2007 | Naasani | |
| 7,244,498 B2 | 7/2007 | Cook et al. | |
| 7,250,082 B2 | 7/2007 | Jang et al. | |
| 7,253,452 B2* | 8/2007 | Steckel et al. | 257/103 |
| 7,267,875 B2 | 9/2007 | Whiteford et al. | |
| 7,309,525 B2 | 12/2007 | Reiss et al. | |
| 7,311,774 B2 | 12/2007 | Alivisatos et al. | |
| 7,329,369 B2 | 2/2008 | Sato et al. | |
| 7,335,418 B2 | 2/2008 | Sato et al. | |
| 7,361,516 B2 | 4/2008 | Uyeda et al. | |
| 7,364,919 B2 | 4/2008 | Pendades et al. | |
| 7,368,086 B2 | 5/2008 | Naasani | |
| 7,374,807 B2 | 5/2008 | Parce et al. | |
| 7,387,833 B2 | 6/2008 | Reiss et al. | |
| 7,416,784 B2 | 8/2008 | Mitsunaga et al. | |
| 7,422,790 B1 | 9/2008 | Scher et al. | |
| 7,459,145 B2 | 12/2008 | Bao et al. | |
| 7,488,819 B2 | 2/2009 | Manabe et al. | |
| 7,589,240 B2 | 9/2009 | Emrick et al. | |
| 7,662,313 B2 | 2/2010 | Whiteford et al. | |
| 7,989,153 B2 | 8/2011 | Skipor et al. | |
| 2002/0016306 A1 | 2/2002 | Hutchison et al. | |
| 2002/0020830 A1 | 2/2002 | Bass et al. | |
| 2002/0146590 A1 | 10/2002 | Matsuo et al. | |
| 2003/0042850 A1 | 3/2003 | Bertram et al. | |
| 2003/0059635 A1 | 3/2003 | Naasani | |
| 2003/0091933 A1 | 5/2003 | Kunita | |
| 2004/0023010 A1 | 2/2004 | Bulovic et al. | |
| 2004/0023261 A1* | 2/2004 | Bruchez et al. | 435/6 |
| 2004/0048241 A1* | 3/2004 | Freeman et al. | 435/5 |
| 2004/0105980 A1 | 6/2004 | Sudarshan et al. | |
| 2004/0110002 A1 | 6/2004 | Kim et al. | |
| 2004/0137263 A1 | 7/2004 | Burn et al. | |
| 2004/0146560 A1 | 7/2004 | Whiteford et al. | |
| 2004/0265571 A1* | 12/2004 | Schwartz et al. | 428/333 |
| 2005/0058416 A1 | 3/2005 | Lee et al. | |
| 2005/0129947 A1* | 6/2005 | Peng et al. | 428/403 |
| 2005/0214536 A1 | 9/2005 | Schrier et al. | |
| 2005/0214967 A1 | 9/2005 | Scher et al. | |
| 2005/0258418 A1* | 11/2005 | Steckel et al. | 257/40 |
| 2005/0265922 A1 | 12/2005 | Nie et al. | |
| 2005/0266246 A1* | 12/2005 | Reiss et al. | 428/403 |
| 2006/0040103 A1 | 2/2006 | Whiteford et al. | |
| 2006/0068506 A1 | 3/2006 | Uyeda et al. | |
| 2006/0083694 A1 | 4/2006 | Kodas et al. | |
| 2006/0128845 A1 | 6/2006 | Emrick et al. | |
| 2006/0130741 A1 | 6/2006 | Peng et al. | |
| 2006/0216508 A1 | 9/2006 | Denisyuk et al. | |
| 2006/0216510 A1 | 9/2006 | Denisyuk et al. | |
| 2006/0216759 A1 | 9/2006 | Naasani et al. | |
| 2007/0034833 A1 | 2/2007 | Parce et al. | |
| 2007/0036962 A1 | 2/2007 | Sasaki et al. | |
| 2007/0072979 A1 | 3/2007 | Moad et al. | |
| 2007/0103068 A1* | 5/2007 | Bawendi et al. | 313/506 |
| 2007/0131905 A1 | 6/2007 | Sato et al. | |
| 2007/0269904 A1 | 11/2007 | Uyeda et al. | |
| 2008/0001167 A1* | 1/2008 | Coe-Sullivan et al. | 257/146 |
| 2008/0038361 A1 | 2/2008 | Cheon et al. | |
| 2008/0085088 A1 | 4/2008 | Lin et al. | |
| 2008/0089836 A1 | 4/2008 | Hainfeld | |
| 2008/0103219 A1 | 5/2008 | Petruska et al. | |
| 2008/0144333 A1 | 6/2008 | Gourlay | |
| 2009/0152567 A1 | 6/2009 | Comerford et al. | |
| 2009/0162011 A1* | 6/2009 | Coe-Sullivan et al. | 385/31 |
| 2009/0181478 A1* | 7/2009 | Cox et al. | 438/22 |
| 2009/0215208 A1* | 8/2009 | Coe-Sullivan et al. | 438/22 |
| 2009/0215209 A1* | 8/2009 | Anc et al. | 438/22 |
| 2009/0251759 A1* | 10/2009 | Domash et al. | 359/288 |
| 2009/0278141 A1* | 11/2009 | Coe-Sullivan et al. | 257/89 |
| 2009/0283743 A1* | 11/2009 | Coe-Sullivan et al. | 257/9 |
| 2009/0283778 A1* | 11/2009 | Coe-Sullivan et al. | 257/88 |
| 2010/0001256 A1* | 1/2010 | Coe-Sullivan et al. | 257/13 |
| 2010/0027192 A1 | 2/2010 | Perry et al. | |
| 2010/0044635 A1* | 2/2010 | Breen et al. | 252/301.6 S |
| 2010/0044636 A1* | 2/2010 | Ramprasad et al. | 252/301.6 S |
| 2010/0051870 A1* | 3/2010 | Ramprasad | 252/301.33 |
| 2010/0051901 A1* | 3/2010 | Kazlas et al. | 257/13 |
| 2010/0051917 A1 | 3/2010 | Kippelen et al. | |
| 2010/0052512 A1* | 3/2010 | Clough et al. | 313/498 |
| 2010/0068468 A1* | 3/2010 | Coe-Sullivan et al. | 428/172 |
| 2010/0132770 A1 | 6/2010 | Beatty et al. | 136/252 |
| 2010/0265307 A1* | 10/2010 | Linton et al. | 347/100 |
| 2010/0314646 A1* | 12/2010 | Breen et al. | 257/98 |
| 2011/0049442 A1 | 3/2011 | Schreuder et al. | |
| 2011/0223425 A1 | 9/2011 | Schreuder et al. | |
| 2011/0233483 A1* | 9/2011 | Breen et al. | 252/519.2 |
| 2011/0245533 A1 | 10/2011 | Breen et al. | |

FOREIGN PATENT DOCUMENTS

| | | | |
|---|---|---|---|
| EP | 745646 A1 * | 12/1996 | C08K 9/12 |
| JP | 2002053319 A | 2/2002 | |
| JP | 2002079076 A | 3/2002 | |
| WO | WO 2007143197 | 12/1995 | |
| WO | WO-2007001438 | 1/2007 | |
| WO | WO-2008070028 | 6/2008 | |
| WO | WO-2009002512 | 12/2008 | |
| WO | WO 2009/035657 | 3/2009 | |
| WO | WO 2009/145813 | 12/2009 | |
| WO | WO-2010039897 | 4/2010 | |

OTHER PUBLICATIONS

European Counterpart EP Application No. 08 831 106.3-1223 Communication dated Sep. 22, 2011.
Ichikawa, et al., J. Mater. Chem., 2006, 16, 221-225.
Kazlas, et al., SID Symposium Digest of Technical Papers—May 2007, vol. 38, Issue 1, pp. 856-859.
Kopping, et al., J. Am. Chem. Soc., Published on web: Apr. 5, 2008.
Lorenz, et al., J. Am Chem. Soc. 1998, 120, 10970-10975.
Murase, et al., Mater. Res. Soc. Symp. Proc. vol. 847 2005, EE13.25.1-EE13.25.5.
Murray, et al., Annu. Rev. Mat. Sci., 30, 545-610 (2000).
Murray et al., J. Am. Chem. Soc., 1993, 115, 8706.
Pudzer, et al. Nano Letters Oct. 27, 2004.
Shandryuk, et al Macromolecules, 2008, 41, 2178-2185.
Steckel, Jonathan S., Thesis entitled "The Synthesis of Inorganic Semiconductor Nanocrystalline Materials For the Purpose of Creating Hybrid Organic/Inorganic Light-Emitting Devices", Massachusetts Institute of Technology, Sep. 2006.
Steigerwald, et al., Annu. Mater. Sci. 1989, 19, 471-495.
Talapin, et al., Nano Letters 2001, vol. 1, No. 4 207-211.
Van Embden, et al., Langmuir 2005, 21, 10226-10233.
Wang, et al., Nano Letters, "Trouble with TOPO; Identification of Adventitious Impurities Beneficial to the Growth of Cadmium Selenide Quantum Dots, Rods, and Wires", Printed on web: Aug. 29, 2008.
Kopping, et al., J. Am. Chem. Soc., Supporting Info. 2008.
PCT/US2008/07901 Search Report and Written Opinion—QD Vision, Inc., mailed Jan. 21, 2009.
Wang, et al., Nano Letters—Supporting Info. 2008.
European Counterpart EP Application No. 08 831 106.3-1223, Summons to attend oral proceedings pursuant to Rule 115(1) EPC, dated Oct. 19, 2012.

(56) References Cited

OTHER PUBLICATIONS

European Counterpart EP Application No. 08 831 106.3-1223, Result of Consultation, dated Jan. 16, 2013.

European Counterpart EP Application No. 08 831 106.3-1223, Brief Communication regarding cancellation of summons to attend oral proceedings, dated Jan. 17, 2103.

Kopping, et al., J. Am. Chem. Soc., Supporting Information, available on J. Am. Chem. Soc. Website upon publication of Kopping, et al., J. Am. Chem. Soc., on web: Apr. 5, 2008.

PCT/US2007/13152 Search Report and Written Opinion—QD Vision, Inc., mailed Jul. 18, 2008.

PCT/US2007/24750 Search Report and Written Opinion—QD Vision, Inc., mailed Apr. 22, 2008.

PCT/US2008/07901 Search Report and Written Opinion—QD Vision, Inc., mailed Jan. 22, 2009.

PCT/US2008/07902 Search Report and Written Opinion—QD Vision, Inc., mailed Sep. 11, 2008.

PCT/US2008/10651 Search Report and Written Opinion—QD Vision, Inc., mailed Dec. 5, 2008.

PCT/US2009/04345 Search Report and Written Opinion—QD Vision, Inc., mailed Oct. 5, 2009.

PCT/US2009/04354 Search Report and Written Opinion—QD Vision, Inc., mailed Oct. 23, 2009.

U.S. Appl. No. 12/655,069—Office Action mailed Nov. 14, 2012.

Wang, et al., Nano Letters—Supporting Information, available on Nano Letters Website upon publication of Wang, et al., Nano Letters, "Trouble with TOPO; Identification of Adventitious Impurities Beneficial to the Growth of Cadmium Selenide Quantum Dots, Rods, and Wires", on web: Aug. 29, 2008.

EPO Communication under rule 71(3) mailed Sep. 20, 2013, in counterpart European Patent Application No. 08 831 106.3.

Japanese Office Action mailed Aug. 27, 2013, in counterpart Japanese Patent Application No. 2010-524868.

Notice of Allowance, mailed Jan. 27, 2014, in copending U.S. Appl. No. 12/655,069, filed Dec. 22, 2009.

Nonfinal Office Action, mailed Nov. 6, 2013, in copending U.S. Appl. No. 13/015,651, filed Jan. 28, 2011.

Nonfinal Office Action, mailed Nov. 7, 2013, in copending U.S. Appl. No. 13/015,670, filed Jan. 28, 2011.

Final Office Action, mailed Apr. 30, 2014, in copending U.S. Appl. No. 13/015,651, filed Jan. 28, 2011.

Final Office Action, mailed May 1, 2014, in copending U.S. Appl. No. 13/015,670, filed Jan. 28, 2011.

\* cited by examiner

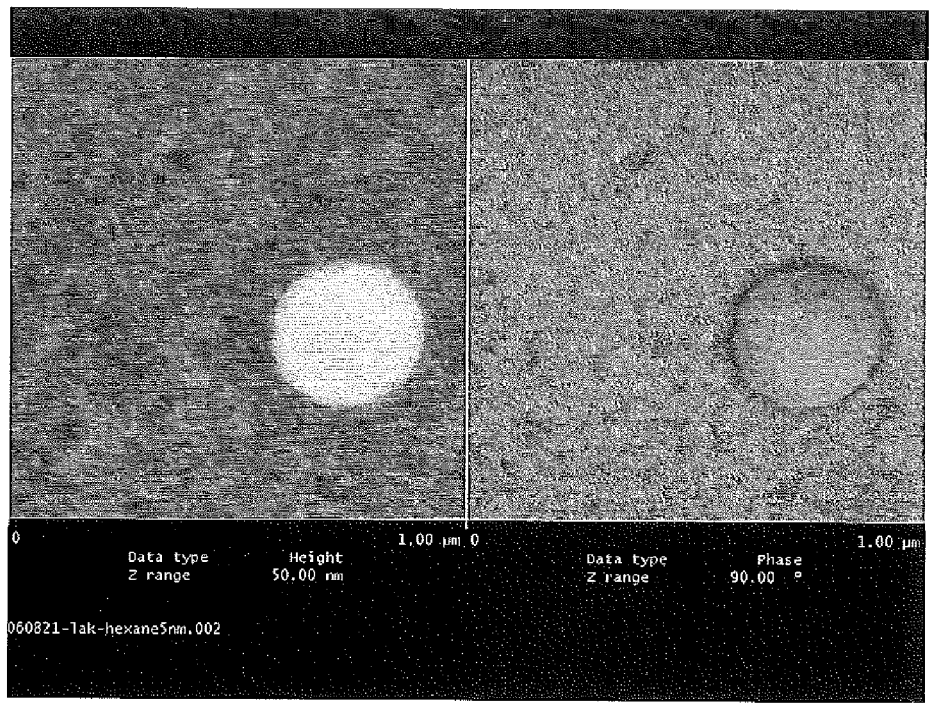
Figure 2: 5 nm CBP thermally evaporated on an aliphatic ligand quantum dot monolayer
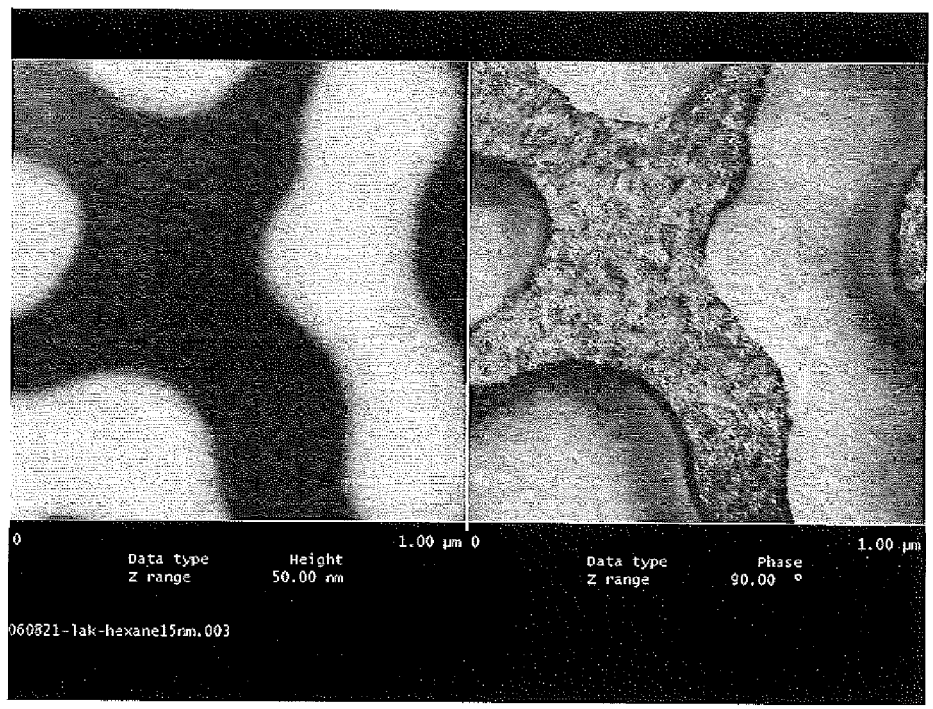
Figure 3: 15 nm CBP thermally evaporated on an aliphatic ligand quantum dot monolayer

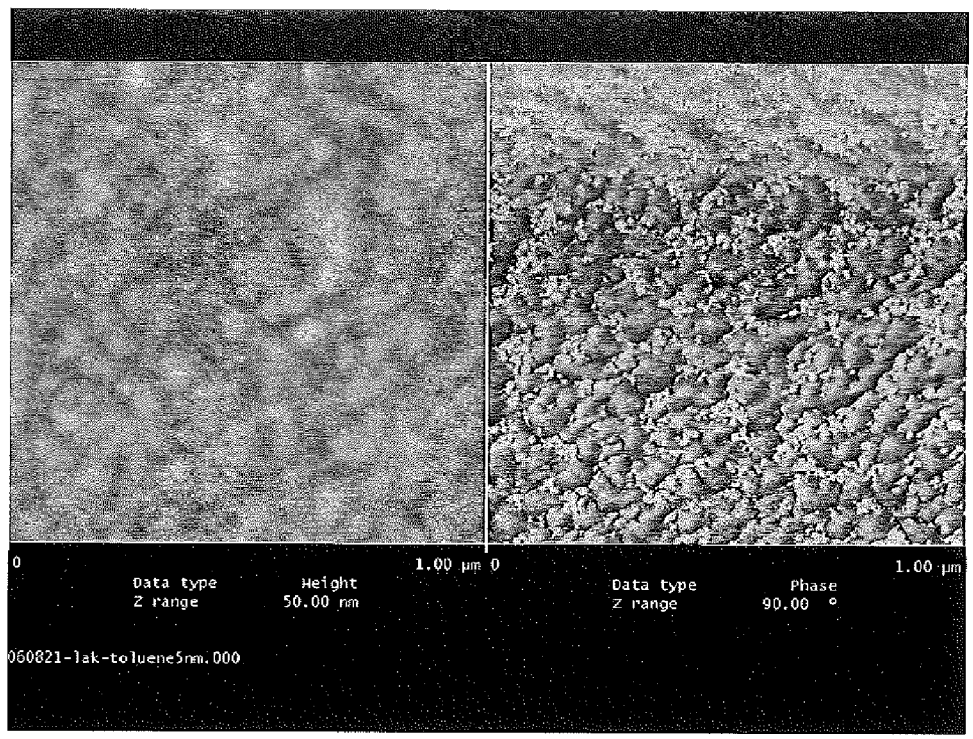
Figure 4: 5 nm CBP thermally evaporated on an aromatic ligand quantum dot monolayer
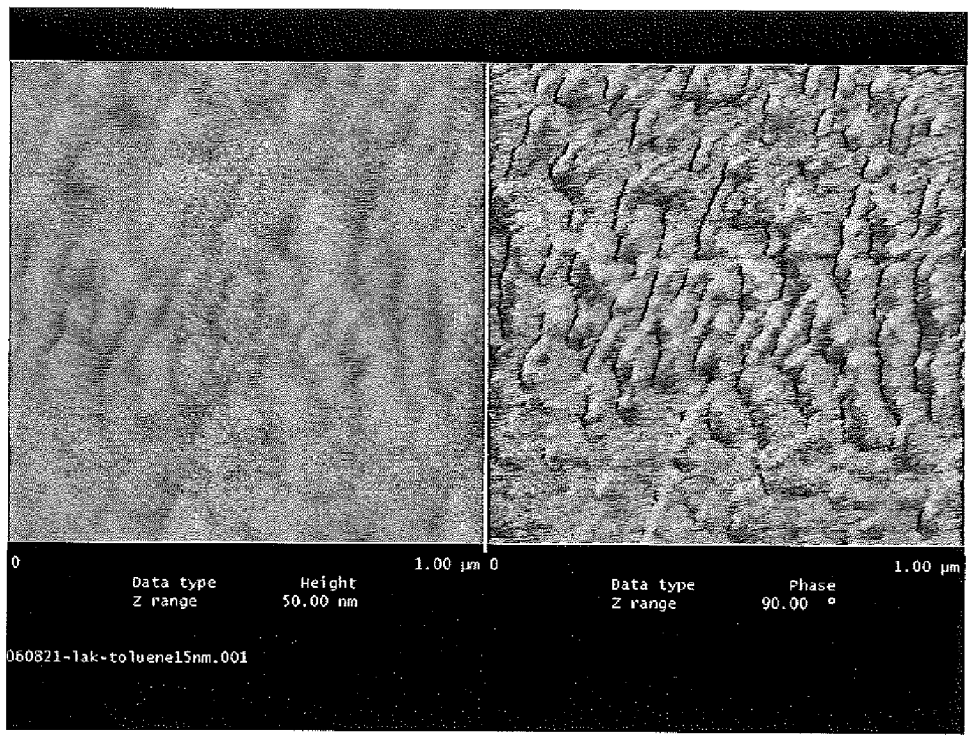
Figure 5: 15 nm CBP thermally evaporated on an aromatic ligand quantum dot monolayer

FUNCTIONALIZED NANOPARTICLES AND METHOD

This application is a continuation of commonly owned International Application No. PCT/US2008/010651 filed 12 Sep. 2008, which was published in the English language as PCT Publication No. WO 2009/035657 on 19 Mar. 2009, which International Application claims priority to U.S. Application No. 60/971,887, filed 12 Sep. 2007; 60/992,598, filed 5 Dec. 2007; and 61/083,998, filed 28 Jul. 2008; each of the foregoing hereby being incorporated herein by reference in its entirety.

International Application No, PCT/US2008/010651 further claims priority to U.S. Application No. 60/971,885, filed 12 Sep. 2007; 60/973,644, filed 19 Sep. 2007; and 61/016,227, filed 21 Dec. 2007. International Application No. PCT/US2008/010651 is also a continuation-in-part application of commonly owned International Application No. PCT/US2007/024750, filed 3 Dec. 2007. International Application No. PCT/US2008/010651 is also a continuation-in-part application of commonly owned International Application No, PCT/US2008/007902, filed 25 Jun. 2008. International Application No. PCT/US2008/010651 is also a continuation-in-part application of commonly owned International Application No. PCT/US2007/013152, filed 4 Jun. 2007, which was published in the English language as PCT Publication No. WO 2007/143197 on 13 Dec. 2007. PCT Application No. PCT/US2007/013152 claims priority from commonly owned U.S. Patent Application Nos.: 60/810,767 filed 2 Jun. 2006, 60/810,914 filed 5 Jun. 2006, 60/804,921 filed 15 Jun. 2006, 60/825,373 filed 12 Sep. 2006, 60/825,374 filed 12 Sep. 2006, 60/825,370 filed 12 Sep. 2006, and 60/886,261 filed 23 Jan. 2007.

TECHNICAL FIELD

The present invention relates to the technical field of nanoparticles and more particularly nanoparticles including ligands and related methods.

BACKGROUND

A predominant method for the synthesis of colloidal quantum dots involves reactions done in high boiling solvents, such as trioctylphosphine oxide (TOPO), trioctylphosphine (TOP), aliphatic phosphonic or carboxylic acids, and aliphatic amine species. The ligand capping groups on the surface of the quantum dots are, therefore, believed to be a statistical distribution of TOPO, TOP, acid, and amine. Throughout the quantum dot literature, in order to affect surface chemistry changes on a particular quantum dot sample (e.g. making water-soluble quantum dots), typical procedures involve cap exchange reactions, whereby already synthesized quantum dots (core or core-shell) are placed in a solution of another ligand and heated for an extended period of time in order to drive off the existing ligands and replace them with the alternate species. These procedures can be detrimental to maintaining the optical properties of the quantum dots and often result in drastically reduced emission efficiencies and stability.

Alternative techniques utilize self-assembled micelles that surround and inter-digitate with the native quantum dot surface ligands. The drawback of these methods include the requirement for polar solvent environments to generate the encapsulating micelle, and thus limiting the technique to aqueous based applications, such as biological tagging and imaging.

Thus, there remains a need for a semiconductor nanocrystal including functionalized ligands that are compatible with an organic based solvent system, and methods for preparing same.

SUMMARY OF THE INVENTION

The present invention relates to nanoparticles including one or more ligands attached to a surface of the nanoparticle. The present invention also relates to methods for preparing a nanoparticle in the presence of one or more ligands.

In accordance with one aspect of the present invention, there is provided a nanoparticle including one or more chemically distinct native ligands attached to a surface thereof, at least one of said ligands being represented by the formula:

wherein X represents a primary amine group, a secondary amine group, a urea, a thiourea, an imidizole group, an amide group, a phosphonic or arsonic acid group, a phosphinic or arsinic acid group, a phosphate or arsenate group, a phosphine or arsine oxide group; Sp represents a spacer group, such as a group capable of allowing a transfer of charge or an insulating group; and Z represents: (i) a reactive group capable of communicating specific chemical properties to the nanoparticle as well as provide specific chemical reactivity to the surface of the nanoparticle, and/or (ii) a group that is cyclic, halogenated, and/or polar a-protic, wherein Z in all cases is not reactive upon exposure to light.

As used herein, "native ligand" refers to a ligand that attaches or coordinates to a nanoparticle surface during the growth or overcoating thereof. Ligands are considered chemically distinct when they have different chemical compositions.

In certain embodiments, Z does not render the nanoparticle dispersible in a liquid medium that includes water.

In certain embodiments, a reactive group can comprise a functional, bifunctional, or polyfunctional reagent, and/or a reactive chemical group.

As used herein, "reactive chemical group" refers to a chemical group that can react with one or more other groups or species. Examples of reactive chemical groups include functional substituent groups. Examples of functional substituent groups include, but are not limited to, thiol, carboxyl, hydroxyl, amino, amine, sulfo, bifunctional groups, polyfunctional groups, etc.)

In certain embodiments, a cyclic group can comprise a saturated or unsaturated cyclic (including, but not limited to, a single ring, a bicyclic structure, a multi-cyclic structure, etc.) compound or aromatic compound. In certain embodiments, the cyclic group can include at least one hetero-atom. In certain embodiments, the cyclic group can include at least one substituent group (including, for example, but not limited to, a reactive chemical group, an organic group (alley, aryl, etc.), etc.). Other examples of cyclic groups are provided herein.

In certain embodiments, a halogenated group can comprise a fluorinated group, a perfluorinated group, a chlorinated group, a perchlorinated group, a brominated group, a perbrominated group, an iodinated group, a periodinated group, etc. Other examples of halogenated groups are provided herein.

In certain embodiments, a polar a-protic group can comprise a ketone, aldehyde, amide, urea, urethane, or an imine. Other examples of polar a-protic groups are provided herein.

In certain embodiments, a nanoparticle can comprise a semiconductor material.

In certain embodiments, a nanoparticle can comprise a core comprising a first material and a shell (or coating material) disposed over at least a portion of a surface of the core, the shell comprising a second material. In certain embodiments, the first material comprises a semiconductor material. In certain embodiments, the second material comprises a semiconductor material. In certain embodiments, one or more additional shells are disposed over at least a portion of a surface of the shell.

In certain preferred embodiments, a nanoparticle comprises a semiconductor nanocrystal. (A semiconductor nanocrystal is also referred to herein as a quantum dot.) In certain embodiments, the semiconductor nanocrystal can comprise a core comprising a first material and a shell (or coating material) disposed over at least a portion of a surface of the core, the shell comprising a second material. Preferably, the second material comprises a nanocrystalline semiconductor material. In certain embodiments, one or more additional shells are disposed over at least a portion of a surface of the shell. Additional discussion of nanoparticles and semiconductor nanocrystals is provided elsewhere herein.

Preferred ligands comprise benzylphosphonic acid, benzylphosphonic acid including at least one substituent group on the ring of the benzyl group, a conjugate base of such acids, and mixtures including one or more of the foregoing. In certain embodiments, a ligand comprises 4-hydroxybenzylphosphonic acid, a conjugate base of the acid, or a mixture of the foregoing. In certain embodiments, a ligand comprises 3,5-di-tert-butyl-4-hydroxybenzylphosphonic acid, a conjugate base of the acid, or a mixture of the foregoing.

Other preferred ligands include ligands being represented by the formula X-Sp-Z comprising an organic amine including a terminal hydroxyl group or a fluorinated organic amine, In certain preferred embodiments, a nanoparticle comprises a semiconductor nanocrystal core comprising a first semiconductor material having an overcoating material comprising a second semiconductor material disposed on at least a portion of a surface of the core, wherein the overcoating material is grown thereon in the presence of one or more of the ligands described herein.

In certain embodiments, a nanoparticle can include two or more chemically distinct native ligands attached to a surface thereof, at least one of said ligands being represented by the formula:

X-Sp-Z, wherein X, Sp, and Z are as described herein.

In certain embodiments, a nanoparticle can include two or more chemically distinct ligands attached to a surface thereof, a first ligand is represented by the formula:

N-Sp-Z wherein N represents a primary amine group, a secondary amine group, an imidizole group, an amide group; and
a second ligand is represented by the formula:

Y-Sp-Z wherein Y represents a phosphonic or arsonic acid group, a phosphinic or arsinic acid group, a phosphate or arsenate group, a phosphine or arsine oxide group; and
wherein Sp, and Z are as described herein, and wherein each of Sp and Z on the first ligand and on the second ligand can be the same or different.

In certain embodiments, Z does not render the nanoparticle dispersible in a liquid medium that includes water.

The nanoparticle can be as described above and elsewhere herein.

Preferred ligands include benzylphosphonic acid, benzylphosphonic acid including at least one substituent group on the ring of the benzyl group, a conjugate base of such acids, and mixtures including one or more of the foregoing. In certain embodiments, a ligand comprises 4-hydroxybenzylphosphonic acid, a conjugate base of the acid, and a mixture of the foregoing. In certain embodiments, a ligand comprises 3,5-di-tert-butyl-4-hydroxybenzylphosphonic acid, a conjugate base of the acid, or a mixture of the foregoing.

Other preferred ligands include ligands being represented by the formula X-Sp-Z comprising an organic amine including a terminal hydroxyl group or a fluorinated organic amine.

In accordance with another aspect of the present invention, there is provided a method for functionalizing a nanoparticle. The method comprises reacting precursors for forming a nanoparticle having a predetermined composition in the presence of one or more chemically distinct ligands, at least one of the ligands being represented by the formula:

X-Sp-Z wherein X represents a primary amine group, a secondary amine group, an imidizole group, an amide group, a phosphonic or arsonic acid group, a phosphinic or arsinic acid group, a phosphate or arsenate group, a phosphine or arsine oxide group; Sp represents a spacer group, such as a group capable of allowing a transfer of charge or an insulating group; and Z represents: (i) a reactive group capable of communicating specific chemical properties to the nanoparticle as well as provide specific chemical reactivity to the surface of the nanoparticle and/or (ii) a group that is cyclic, halogenated, and/or polar a-protic, wherein Z in all cases is not reactive upon exposure to light.

In certain embodiments, Z does not render the nanoparticle dispersible in a liquid medium that includes water.

In certain embodiments, a reactive group can comprise a functional, bifunctional, or polyfunctional reagent, and/or a reactive chemical group.

In certain embodiments, a cyclic group can comprise a saturated or unsaturated cyclic (including, but not limited to, a single ring, a bicyclic structure, a multi-cyclic structure, etc.) compound or aromatic compound. In certain embodiments, the cyclic group can include at least one hetero-atom. In certain embodiments, the cyclic group can include at least one substituent group (including, for example, but not limited to, a reactive chemical group, an organic group (alky, aryl, etc.), etc.) Other examples of cyclic groups are provided herein.

In certain embodiments, a halogenated group can comprise a fluorinated group, perfluorinated group, a chlorinated group, a perchlorinated group, a brominated group, a perbrominated group, an iodinated group, a periodinated group, etc. Other examples of halogenated groups are provided herein.

In certain embodiments, a polar a-protic group can comprise a ketone, aldehyde, amide, urea, urethane, or an imine. Other examples of polar a-protic groups are provided herein.

In certain embodiments, the predetermined composition of the nanoparticle comprises a semiconductor material.

In certain preferred embodiments, the predetermined composition comprises one or more metals and one or more chalcogens or pnictogens In certain embodiments, precursors include one or more metal-containing precursors and one or more chalcogen-containing or pnictogen-containing precursors.

In certain embodiments, a nanoparticle can comprise a core comprising a first material and a shell (or coating material)

disposed over at least a portion of a surface of the core, the shell comprising a second material. In certain embodiments, the first material comprises a semiconductor material. In certain embodiments, the second material comprises a semiconductor material. In certain embodiments, one or more additional shells are disposed over at least a portion of a surface of the shell.

In certain preferred embodiments, a nanoparticle comprises a semiconductor nanocrystal. In certain embodiments, the semiconductor nanocrystal can comprise a core comprising a first material and a shell for coating material) disposed over at least a portion of a surface of the core, the shell comprising a second material. Preferably, the second material comprises a nanocrystalline semiconductor material. In certain embodiments, one or more additional shells are disposed over at least a portion of a surface of the shell.

Preferred ligands include benzylphosphonic acid, benzylphosphonic acid including at least one substituent group on the ring of the benzyl group, a conjugate base of such acids, and mixtures including one or more of the foregoing. In certain embodiments, a ligand comprises 4-hydroxybenzylphosphonic acid, a conjugate base of the acid, and mixtures including one or more of the foregoing. In certain embodiments, a ligand comprises 3,5-di-tert-butyl-4-hydroxybenzylphosphonic acid, a conjugate base of the acid, or a mixture of the foregoing.

Other preferred ligands include ligands being represented by the formula X-Sp-Z comprising an organic amine including a terminal hydroxyl group or a fluorinated organic amine.

In certain embodiments, the precursors are reacted in the presence of two or more chemically distinct ligands, at least one of said ligands being represented by the formula:

X-Sp-Z, wherein X, Sp, and Z are as described herein.

In certain embodiments, the precursors comprise one or more metal-containing precursors and one or more chalcogen-containing precursors or pnictogen-containing precursors.

In certain embodiments, the precursors are reacted in the presence of two or more chemically distinct ligands, wherein a first ligand is represented by the formula:

N-Sp-Z wherein N represents a primary amine group, a secondary amine group, an imidizole group, an amide group; and a second ligand is represented by the formula:

Y-Sp-Z wherein Y represents a phosphonic or arsonic acid group, a phosphinic or arsinic acid group, a phosphate or arsenate group, a phosphine or arsine oxide group; and wherein Sp, and Z are as described herein, and wherein each of Sp and Z on the first ligand and on the second ligand can be the same or different.

In certain embodiments, the precursors comprise one or more metal-containing precursors and one or more chalcogen-containing precursors or pnictogen-containing precursors.

In accordance with another aspect of the present invention, there is provided a method for overcoating at least a portion of a surface of a nanoparticle with a coating material having a predetermined composition, the method comprising reacting precursors for the predetermined composition in the presence of one or more chemically distinct ligands, at least of the ligands being represented by the formula:

X-Sp-Z wherein X represents a primary amine group, a secondary amine group, an imidizole group, an amide group, a phosphonic or arsonic acid group, a phosphinic or arsinic acid group, a phosphate or arsenate group, a phosphine or arsine oxide group; Sp represents a spacer group, such as a group capable of allowing a transfer of charge or an insulating group; and Z represents: (i) a reactive group capable of communicating specific chemical properties to the nanoparticle as well as provide specific chemical reactivity to the surface of the nanoparticle and/or (ii) a group that is cyclic, halogenated, and/or polar a-protic, wherein Z in all cases is not reactive upon exposure to light.

In certain embodiments, Z does not render the nanoparticle dispersible in a liquid medium that includes water.

In certain embodiments, a reactive group can comprise a functional, bifunctional, or polyfunctional reagent, and/or a reactive chemical group.

In certain embodiments, a cyclic group can comprise a saturated or unsaturated cyclic (including, but not limited to, a single ring, a bicyclic structure, a multi-cyclic structure, etc.) compound or aromatic compound. In certain embodiments, the cyclic group can include at least one hetero-atom. In certain embodiments, the cyclic group can include at least one substituent group (including, for example, but not limited to, a reactive chemical group, an organic group (alky, aryl, etc.), etc.). Other examples of cyclic groups are provided herein.

In certain embodiments, a halogenated group can comprise a fluorinated group, perfluorinated group, a chlorinated group, a perchlorinated group, a brominated group, a perbrominated group, an iodinated group, a periodinated group, etc. Other examples of halogenated groups are provided herein.

In certain embodiments, a polar a-protic group can comprise a ketone, aldehyde, amide, urea, urethane, or an imine. Other examples of polar a-protic groups are provided herein.

In certain embodiments, the nanoparticle comprises a semiconductor material.

In certain embodiments, the nanoparticle can comprise a core comprising a first material and a shell (or coating material) disposed over at least a portion of a surface of the core, the shell comprising a second material. In certain embodiments, the first material comprises a semiconductor material. In certain embodiments, the second material comprises a semiconductor material. In certain embodiments, one or more additional shells are disposed over at least a portion of a surface of the shell.

In certain preferred embodiments, a nanoparticle comprises a semiconductor nanocrystal. In certain embodiments, the semiconductor nanocrystal can comprise a core comprising a first material and a shell (or coating material) disposed over at least a portion of a surface of the core, the shell comprising a second material. Preferably, the second material comprises a nanocrystalline semiconductor material. In certain embodiments, one or more additional shells are disposed over at least a portion of a surface of the shell.

In certain embodiments, the predetermined composition of the coating material comprises a semiconductor material, preferably a nanocrystal line semiconductor material.

In certain preferred embodiments, the predetermined composition comprises one or more metals and one or more chalcogens or pnictogens In certain embodiments, precursors include one or more metal-containing precursors and one or more chalcogen-containing or pnictogen-containing precursors.

Preferred ligands include benzylphosphonic acid, benzylphosphonic acid including at least one substituent group on the ring of the benzyl group, a conjugate base of such acids, and mixtures including one or more of the foregoing. In certain embodiments, a ligand comprises 4-hydroxybenzylphosphonic acid, a conjugate base of the acid, and a mixture of the foregoing. In certain embodiments, a ligand comprises 3,5-di-tert-butyl-4-hydroxybenzylphosphonic acid, a conjugate base of the acid, or a mixture of the foregoing.

Other preferred ligands include ligands being represented by the formula X-Sp-Z comprising an organic amine including a terminal hydroxyl group or a fluorinated organic amine.

In certain embodiments, the precursors are reacted in the presence of two or more chemically distinct ligands, at least one of said ligands being represented by the formula:

X-Sp-Z, wherein X, Sp, and Z are as described herein.

In certain embodiments, the precursors are reacted in the present of two or more chemically distinct ligands, wherein a first ligand is represented by the formula:

N-Sp-Z wherein N represents a primary amine group, a secondary amine group, an imidizole group, an amide group; and a second ligand is represented by the formula:

Y-Sp-Z wherein Y represents a phosphonic or arsonic acid group, a phosphinic or arsinic acid group, a phosphate or arsenate group, a phosphine or arsine oxide group; and wherein Sp, and Z are as described herein, and wherein each of Sp and Z on the first ligand and on the second ligand can be the same or different.

In another aspect of the present invention, there is provided a method for preparing nanocrystals comprising a semiconductor material, the method comprising heating a mixture comprising a liquid medium and semiconductor material precursors in the presence of a first ligand compound including an amine group (e.g., N-Sp-Z, wherein N represents a primary amine group, a secondary amine group, an imidizole group, an amide group) and a second ligand compound including an acid group (e.g., Y-Sp-Z, wherein Y represents a phosphonic or arsonic acid group, a phosphinic or arsinic acid group, a phosphate or arsenate group, a phosphine or arsine oxide group). Sp and Z are as described herein.

In certain preferred embodiments the first ligand compound including an amine group and second ligand compound including an acid group are initially present in an equimolar amount, the equimolar amount being determined based on the amine group content of the first ligand compound and the acid group content of the second ligand compound.

In certain embodiments, the first ligand compound is represented by the formula A-L, wherein A is the acid group and L comprises an aryl group, a heteroaryl group, or a straight or branched $C_{1-18}$ hydrocarbon chain. In certain embodiments, the second ligand compound is represented by the formula N-L, wherein N is the amine group and L comprises an aryl group, a heteroaryl group, or a straight or branched $C_{1-18}$ hydrocarbon chain. In certain embodiments, the hydrocarbon chain includes at least one double bond, at least one triple bond, or at least one double bond and one triple bond. In certain embodiments, the hydrocarbon chain is interrupted by —O—, —S—, —N($R_a$)—, —N($R_a$)—C(O)—O—, —O—C(O)—N($R_a$)—, —N($R_a$)—C(O)—N($R_b$)—, —O—C(O)—O—, —P($R_a$)—, or —P(O)($R_a$)—, wherein each of $R_a$ and $R_b$ independently, is hydrogen, alkyl, alkenyl, alkynyl, alkoxy, hydroxylalkyl, hydroxyl, or haloalkyl. In certain embodiments, the aryl group is a substituted or unsubstituted cyclic aromatic group. In certain embodiments, the aryl group includes phenyl, benzyl, naphthyl, tolyl, anthracyl, nitrophenyl, or halophenyl. In certain embodiments, the heteroaryl group comprises an aryl group with one or more heteroatoms in the ring, for instance furyl, pyridyl, pyrrolyl, phenanthryl. In certain embodiments, A comprises a phosphinic acid group or a carboxylic acid group. In certain embodiments, A comprises an oleic acid group or a myristic acid group. In certain preferred embodiments, A comprises a phosphonic acid group.

In certain embodiments of the methods described herein, the method is carried out in a liquid medium. Preferably, the liquid medium comprises a coordinating solvent or mixture of coordinating solvents. Examples of coordinating solvents including those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain aspects and embodiments of the inventions described or contemplated by this general description, the following detailed description, and claims, a nanoparticle can include a core and an overcoating (also referred to herein as a shell). A nanoparticle including a core and shell is also referred to as having a core/shell structure. The shell is disposed over at least a portion of the core. In certain embodiments, the shell is disposed over all or substantially all of the outer surface of the core. In certain embodiments of a nanoparticle including a core/shell structure, the core can comprise a first semiconductor material and the shell can comprise a second semiconductor material. In certain embodiments, the core comprises a semiconductor nanocrystal. In certain embodiments, a nanocrystal can have a diameter of less than about 10 nanometers. In embodiments including a plurality of nanoparticles, the distribution of nanoparticles sizes is preferably monodisperse.

In certain aspects and embodiments of the inventions described or contemplated by this general description, the following detailed description, and claims, a nanoparticle is water insoluble or not dispersible in a liquid medium comprising water.

In certain aspects and embodiments of the inventions described or contemplated by this general description, the following detailed description, and claims, a nanoparticle comprising a semiconductor material (preferably, a semiconductor nanocrystal) is at least partially overcoated with a coating in the presence of one or more of the ligands taught herein. In certain embodiments, the coating comprises more than one material. In certain embodiments including a coating comprising more than one material, the materials are applied sequentially. In certain embodiments, a core can include multiple overcoats or shells disposed on a surface thereof. Each of the multiple overcoats or shells can comprise the same or different composition. In certain aspects and embodiments of the inventions described or contemplated by this general description, the following detailed description, and claims, a method is carried out in a non-aqueous medium. In certain preferred embodiments, the method is a colloidal synthesis method.

The foregoing, and other aspects and embodiments described herein all constitute embodiments of the present invention.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

In the drawings:

FIG. 2 depicts Atomic Force Microscope images showing 5 nm CBP thermally evaporated on an aliphatic ligand quantum dot monolayer.

FIG. 3 depicts Atomic Force Microscope images showing 15 nm CBP thermally evaporated on an aliphatic ligand quantum dot monolayer.

FIG. 4 depicts Atomic Force Microscope images showing 5 nm CBP thermally evaporated on an aromatic ligand quantum dot monolayer.

FIG. 5 depicts Atomic Force Microscope images showing the effect of ligand composition on semiconductor nanocrystal layer interface morphology.

Figure 1:
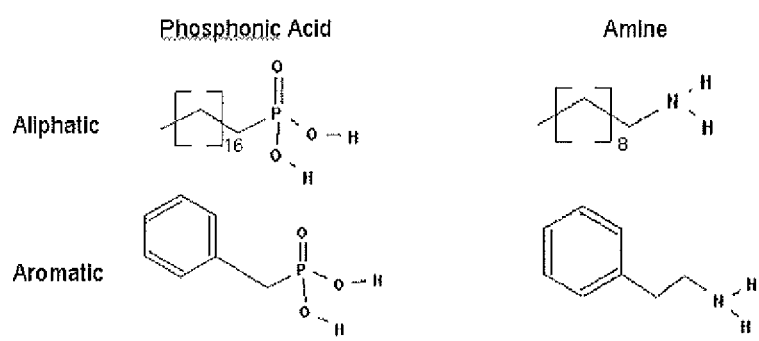
FIG. 1 represents the chemical structures of examples of certain compositions useful in carrying out the present invention.

The attached figures are simplified representations presented for purposes of illustration only; the actual structures may differ in numerous respects, including, e.g., relative scale, etc.

For a better understanding to the present invention, together with other advantages and capabilities thereof, reference is made to the following disclosure and appended claims in connection with the above-described drawings.

DETAILED DESCRIPTION OF THE INVENTION

In accordance with certain embodiments of the present invention there is provided a nanoparticle including a ligand attached to a surface thereof, the ligand being represented by the formula:

X-Sp-Z wherein:

X represents a primary amine group, a secondary amine group, a urea, a thiourea, an imidizole group, an amide group, a phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents: (i) a reactive group capable of communicating specific chemical properties to the nanocrystal as well as provide specific chemical reactivity to the surface of the nanocrystal, and/or (ii) a group that is cyclic, halogenated, or polar a-protic. The ligand attaches or coordinates to a surface of the nanoparticle during formation or overcoating thereof.

Examples of Sp include, but are not limited to, straight or branched $C_1$-$C_{18}$ hydrocarbon chains. In certain embodiments, the hydrocarbon chain includes at least one double bond, at least one triple bond, or at least one double bond and one triple bond. In certain embodiments, the hydrocarbon chain is interrupted by —O—, —S—, —N($R_a$)—, —N($R_a$)—C(O)—O—, —O—C(O)—N($R_a$)—, —N($R_a$)—C(O)—N($R_b$)—, —O—C(O)—O—, —P($R_a$)—, or —P(O)($R_a$)—, wherein each of $R_a$ and $R_b$, independently, is hydrogen, alkyl, alkenyl, alkynyl, alkoxy, hydroxylalkyl, hydroxyl, or haloalkyl.

Examples of reactive groups include, without limitation, functional, bifunctional, and polyfunctional reagents (e.g., homobifunctional or heterobifunctional), and reactive chemical groups (e.g., thiol, or carboxyl, hydroxyl, amino, amine, sulfo, and the like). Examples of additional reactive groups include carbodithioate, carbodithioic acid, thiourea, amide, phosphine oxide, phosphonic or phosphinic acid, thiophosphonic or thiophosphinic acid, which can be substituted with alkyl and/or aryl units that are perhalogenated or partially halogenated. Examples of cyclic groups include, but are not limited to, saturated or unsaturated cyclic or bicyclic compounds (e.g. cyclohexyl, isobornyl, etc.), or aromatic compounds (e.g. phenyl, benzyl, naphthyl, biphenyl, fluorenyl, triarylamine, etc.). In certain embodiments, a cyclic group can include one or more substituent groups (including, for example, but not limited to, a reactive chemical group, an organic group (alky, aryl, etc.), etc.). Halogenated groups include, but are not limited to, fluorinated groups, perfluorinated groups, (e.g. perfluoroalkyl, perfluorophenyl, perfluoroamines, etc.), chlorinated groups, perchlorinated groups. Examples of polar a-protic groups include, but are not limited to, ketones, aldehydes, amides, ureas, urethanes, imines, etc.

In certain embodiments, the group comprising Z imparts predetermined chemical miscibility properties to the semiconductor nanocrystal to which it is attached.

In certain embodiments, Z does not include a non-functionalized straight or branched $C_1$-$C_{18}$ hydrocarbon chain.

In certain embodiments, the nanoparticle comprises a semiconductor nanoparticle. In certain preferred embodiments, the nanoparticle comprises a semiconductor nanocrystal.

In accordance with certain embodiments, there is provided a nanoparticle including two or more chemically distinct ligands attached to a surface thereof, at least one of said ligands being represented by the formula:

X-Sp-Z wherein:

X represents a primary amine group, a secondary amine group, a urea, a thiourea, an imidizole group, an amide group, phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents: (i) a reactive group capable of communicating specific chemical properties to the nanocrystal as well as provide specific chemical reactivity to the surface of the nanocrystal, and/or (ii) group that is cyclic, halogenated, or polar a-protic.

Examples of Sp and Z include, without limitation, those described herein.

In certain embodiments, Z does not include a non-functionalized straight or branched $C_1$-$C_{18}$ hydrocarbon chain.

In certain embodiments, the nanoparticle comprises a semiconductor nanoparticle. In certain preferred embodiments, the nanoparticle comprises a semiconductor nanocrystal.

In accordance with certain embodiments there is provided a nanoparticle including two or more chemically distinct ligands attached to a surface thereof, wherein a first ligand is represented by the formula:

N-Sp-Z wherein:

N represents a primary amine group, a secondary amine group, a urea, a thiourea, an imidizole group, an amide group, or other nitrogen containing functional group;

Sp represents a spacer group, such as a group capable of allowing a transfer of charge or an insulating group; and Z represents a reactive group capable of communicating specific chemical properties to the nanocrystal and/or provide specific chemical reactivity to the surface of the nanocrystal; and a second ligand is represented by the formula:

Y-Sp-Z wherein:

Y represents a phosphonic or arsonic acid group, a phosphinic or arsinic acid group, a phosphate or arsenate group, a phosphine or arsine oxide group, or other phosphorous-containing or arsenic-containing functional group;

Sp represents a spacer group, such as a group capable of allowing a transfer of charge or an insulating group; and Z represents a reactive group capable of communicating specific chemical properties to the nanocrystal and/or provide specific chemical reactivity to the surface of the nanocrystal.

Examples of Sp and Z for inclusion in N-Sp-Z and P-Sp-Z include, without limitation, those described herein. Sp and Z can be independently selected. Sp and Z included in each of the two ligands can be the same or different.

In certain embodiments, Z does not include a non-functionalized straight or branched $C_1$-$C_{18}$ hydrocarbon chain.

In certain embodiments, the nanoparticle comprises a semiconductor nanoparticle. In certain preferred embodiments, the nanoparticle comprises a semiconductor nanocrystal.

In accordance with another embodiment of the invention, there is provided a method for functionalizing a nanoparticle. The method comprises reacting precursors for forming a nanoparticle having a predetermined composition in the presence of the herein described ligand X-Sp-Z, wherein X, Sp, and Z are as described herein.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition.

In certain embodiments, the method is carried out in a liquid medium. Preferably, the liquid medium comprises a coordinating solvent or mixture of coordinating solvents. Examples of coordinating solvents including those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain embodiments, the mole ratio of total metal included in the one or more metal-containing precursors to total moles of ligand represented by the formula X-Sp-Z is in the range from about 1:0.1 to about 1:100. In certain embodiments, the mole ratio of total moles of metal included in the one or more metal-containing precursors to total moles of ligand represented by the formula X-Sp-Z is in the range from about 1:1 to about 1:50. In certain embodiments, the mole ratio of total moles of metal included in the one or more metal-containing precursors to total moles of ligand represented by the formula X-Sp-Z is in the range from about 1:1 to about 1:30.

In certain embodiments in which the method is carried out in a liquid medium, the mole ratio of total moles of the liquid medium to total moles of ligand represented by the formula X-Sp-Z is in the range from about 500:1 to about 2:1. In certain embodiments, the mole ratio of total moles of the liquid medium to total moles of ligand represented by the formula X-Sp-Z is in the range from about 100:1 to about 5:1. In certain embodiments, the mole ratio of total moles of the liquid medium to total moles of ligand represented by the formula X-Sp-Z is in the range from about 50:1 to about 5:1.

In accordance with certain embodiments, there is provided a method for functionalizing nanoparticle. The method comprises reacting precursors for forming a nanoparticle having a predetermined composition in the presence of two or more chemically distinct ligands, at least one of said ligands being represented by the formula:

X-Sp-Z wherein:

X represents a primary amine group, a secondary amine group, a urea, a thiourea, an imidizole group, an amide group, phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents: (i) a reactive group capable of communicating specific chemical properties to the nanocrystal as well as provide specific chemical reactivity to the surface of the nanocrystal, and/or (ii) a group that is cyclic, halogenated, or polar a-protic.

In certain embodiments, Z does not include a non-functionalized straight or branched $C_1$-$C_{18}$ hydrocarbon chain. Examples of Sp and Z include, without limitation, those described herein.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition.

In certain embodiments there is provided a method for functionalizing a nanoparticle. The method comprises reacting precursors for forming a nanoparticle having a predetermined composition in the presence of two or more chemically distinct ligands, wherein a first ligand is represented by the formula:

N-Sp-Z wherein:

N represents a primary amine group, a secondary amine group, a urea, a thiourea, an imidizole group, an amide group;

Sp represents a spacer group, such as a group capable of allowing a transfer of charge or an insulating group; and Z represents a reactive group capable of communicating specific chemical properties to the nanocrystal as well as provide specific chemical reactivity to the surface of the nanocrystal; and a second ligand is represented by the formula:

Y-Sp-Z wherein:

Y represents phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents a reactive group capable of communicating specific chemical properties to the nanocrystal as well as provide specific chemical reactivity to the surface of the nanocrystal.

Examples of Sp and Z include, without limitation, those described herein. Sp and Z can be independently selected. Sp and Z included in each of the two ligands can be the same or different.

In certain embodiments, the nanoparticle comprises a semiconductor nanoparticle. In certain preferred embodiments, the nanoparticle comprises a semiconductor nanocrystal. In certain embodiments, the predetermined precursors include a metal-containing precursor and a chalcogen-containing or pnictogen-containing precursor. The precursors are preferably included in the reaction mixture in amounts based on the predetermined composition. In accordance another embodiment of the invention, there is provided a method for overcoating at least a portion of a surface of a nanoparticle with a coating material having a predetermined composition, the method comprising reacting precursors for the predetermined coating material in the presence of a ligand represented by the formula X-Sp-Z and the nanoparticle to be coated, wherein X, Sp, and Z are as described herein. In certain embodiments, the nanoparticle comprises a semiconductor nanoparticle. In certain preferred embodiments, the nanoparticle comprises a semiconductor nanocrystal. In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In certain embodiments, the method is carried out in a liquid medium. Preferably, the liquid medium comprises a coordinating solvent or mixture of coordinating solvents. Examples of coordinating solvents including those provided herein. Other coordinating solvents can also be used. In certain embodiments, the method can be carried out in a liquid medium comprising a non-coordinating solvent or mixture of non-coordinating solvents. Examples of non-coordinating solvents include, but are not limited to, squalane, octadecane, or any other saturated hydrocarbon molecule. Mixtures of two or more solvents can also be used. Other suitable non-coordinating solvents can be readily ascertained by one of ordinary skill in the art.

In certain embodiments, the mole ratio of total metal included in the nanoparticles being overcoated to total moles of ligand represented by the formula X-Sp-Z is in the range from about 1:0.1 to about 1:100. In certain embodiments, the mole ratio of total moles of metal included in the nanoparticles being overcoated to total moles of ligand represented by the formula X-Sp-Z is in the range from about 1:1 to about 1:50. In certain embodiments, the mole ratio of total moles of metal included in the nanoparticles being overcoated to total moles of ligand represented by the formula X-Sp-Z is in the range from about 1:1 to about 1:30.

In certain embodiments of the method being carried out in a liquid medium, the mole ratio of total moles of the liquid medium to total moles of ligand represented by the formula X-Sp-Z is in the range from about 500:1 to about 2:1. In certain embodiments, the mole ratio of total moles of the liquid medium to total moles of ligand represented by the formula X-Sp-Z is in the range from about 100:1 to about 5:1. In certain embodiments, the mole ratio of total moles of the liquid medium to total moles of ligand represented by the formula X-Sp-Z is in the range from about 50:1 to about 5:1.

In accordance with further embodiments of the invention, there is provided a method for overcoating at least a portion of a surface of a nanoparticle with a coating material having a predetermined composition, the method comprising reacting precursors for the predetermined coating material in the presence of two or more chemically distinct ligands and the nanoparticle to be coated, at least one of said ligands being represented by the formula:

X-Sp-Z and the nanoparticle to be coated, wherein:

X represents a primary amine group, a secondary amine group, a urea, a thiourea, an imidizole group, an amide group, phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents: (i) a reactive group capable of communicating specific chemical properties to the nanocrystal as well as provide specific chemical reactivity to the surface of the nanocrystal, and/or (ii) a group that is cyclic, halogenated, or polar a-protic.

In certain embodiments, Z does not include a non-functionalized straight or branched $C_1$-$C_{18}$ hydrocarbon chain.

Examples of Sp and Z include, without limitation, those described herein.

In certain embodiments, the nanoparticle comprises a semiconductor nanoparticle. In certain preferred embodiments, the nanoparticle comprises a semiconductor nanocrystal. In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In certain embodiments, there is provided a method for overcoating at least a portion of a surface of a nanoparticle with a coating material having a predetermined composition, the method comprising reacting precursors for the predetermined coating material in the presence of two or more chemically distinct ligands and the nanoparticle to be coated, wherein a first ligand is represented by the formula:

N-Sp-Z wherein:

N represents a primary amine group, a secondary amine group, a urea, a thiourea, an imidizole group, an amide group;

Sp represents a spacer group, such as a group capable of allowing a transfer of charge or an insulating group; and Z represents a reactive group capable of communicating specific chemical properties to the nanocrystal as well as provide specific chemical reactivity to the surface of the nanocrystal; and a second ligand is represented by the formula:

Y-Sp-Z wherein Y represents a phosphonic or arsonic acid group, a phosphinic or arsinic acid group, a phosphate or arsenate group, a phosphine or arsine oxide group;

Sp represents a spacer group, such as a group capable of allowing a transfer of charge or an insulating group; and Z represents a reactive group capable of communicating specific chemical properties to the nanocrystal as well as provide specific chemical reactivity to the surface of the nanocrystal.

Examples of Sp and Z include, without limitation, those described herein. Sp and Z can be independently selected. Sp and Z including in the two ligands can be the same or different.

In certain embodiments, the nanoparticle comprises a semiconductor nanoparticle. In certain preferred embodiments, the nanoparticle comprises a semiconductor nanocrystal.

In certain embodiments, the coating composition comprises a semiconductor material. In certain embodiments, the precursors include a metal-containing precursor and a chalcogen-containing or pnictogen-containing precursor. The precursors are preferably included in the reaction mixture in amounts based on the predetermined composition.

In carrying out the methods described herein, the precursors are selected and reacted in amounts and under reaction conditions, and for a period of time, to produce a nanoparticle having the predetermined composition. Such variables can be routinely determined by a person of ordinary skill in the relevant art. In certain embodiments, the reaction is carried out in a controlled atmosphere (substantially free of water moisture and air). In certain preferred embodiments, the reaction is carried out in a water-free inert atmosphere.

In certain embodiments of the present invention, a nanoparticle (e.g., a semiconductor nanocrystal) is formed, or overcoated in order to generate a shell on at least a portion of an outer surface of a nanoparticle, in the presence of at least one molecule having the following formula:

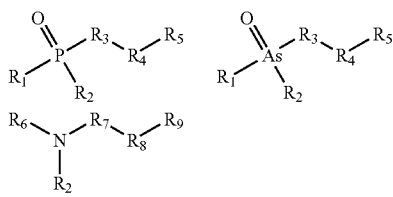

Wherein $R_1$ represents a hydroxyl group; $R_2$ represents a hydroxyl, hydrogen, an alkyl or alkylene group, an aryl or arylene group, $—OR_{11}$, $—NHR_{11}$, $—NR_{11}R_{11}$, $—SR_{11}$, wherein $R_{11}$ represents hydrogen, an alkyl group, or an aryl group; $R_3$ and $R_4$, which can be the same or different, represent a bond, an alkyl or alkylene group, an aryl or arylene group, a fluorocarbon group,

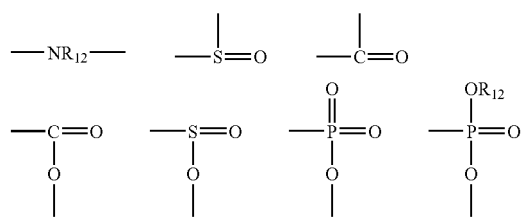

wherein $R_{12}$ is an alkyl or alkylene group or an aryl or arylene group; $R_5$ represents hydrogen, an alkyl group including one or more functional groups, an alkylene group, an aryl or arylene group, $—OR_{13}$, $—NHR_{13}$, $—NR_{13}R_{13}$, $—SR_{13}$, wherein $R_{13}$ represents hydrogen, an alkyl group, or an aryl group; $R_6$ represents hydrogen; $R_7$ represents hydrogen, an alkyl or alkylene group, an aryl or arylene group, $—OR_{14}$, $—NHR_{14}$, $—NR_{14}R_{14}$, $—SR_{14}$, wherein $R_{14}$ represents hydrogen, an alkyl group, or an aryl group; $R_8$ and $R_9$, which can be the same or different, represent a bond, an alkylene group, an aryl or arylene group, a fluorocarbon group,

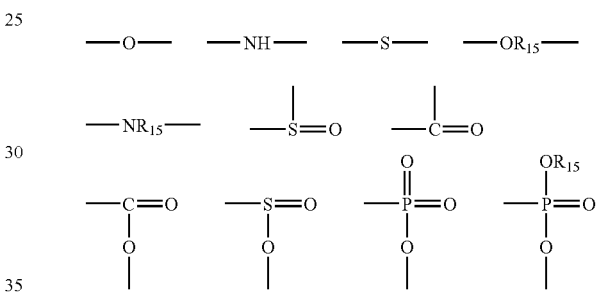

wherein $R_{15}$ is an alkyl or alkylene group or an aryl or arylene group; $R_8$ can also represent an alkyl group; $R_9$ can represent an alkyl group including one or more functional groups; $R_{10}$ represents hydrogen, an alkyl or alkylene group, an aryl or arylene group, $—OR_{16}$, $—NHR_{16}$, $—NR_{16}R_{16}$, $—SR_{16}$, wherein $R_{16}$ represents hydrogen, an alkyl group, or an aryl group.

Furthermore, the architecture described herein opens up the possibility for a modular synthetic scheme for tailoring a quantum dot surface with any desired characteristic. For example, a terminal hydroxyl group provides a site for additional chemical reactivity. The nucleophilic nature of the —OH group can do various addition and substitution reactions with the appropriate electrophile. For example, quantum dots (e.g., semiconductor nanocrystals) with this nucleophilic surface group can be reacted with an electrophile, such as an acid chloride, isocyanate, or carboxylic acid group resulting in the following ester and urethane linkages:

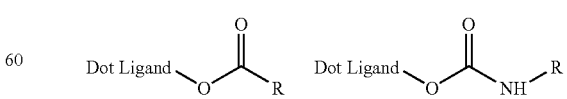

Where R can be any substituent. The —OH group can also be substituted for a primary amine resulting in the following amide and urea linkages with the electrophiles mentioned herein:

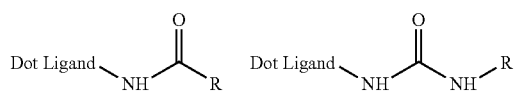

Where, again, R can be any substituent.

Functionalizing Surface of the Semiconductor Nanocrystal with Terminal Hydroxyl Groups Chemical Structures Used:

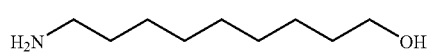

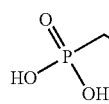

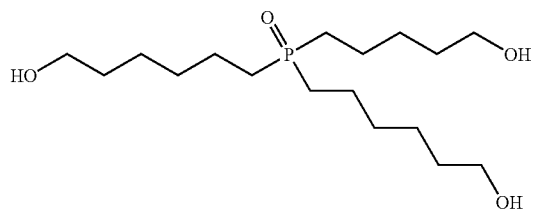

This approach may be achieved in the presence of phosphine oxide (TOPO) with the addition of high boiling polar a-protic solvents (e.g. 1,3-Dimethyl-2-imidazolidone (DMI), Carbitol Acetate, N,N-Dimethylacrylamide (DMAc), 1-Methyl-2-pyrrolidnone (NMP), etc.).

Examples of Coupling Species to Hydroxy-terminated Semiconductor Nanocrystals.

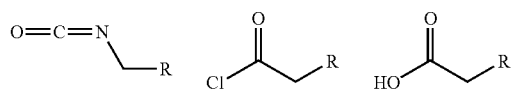

The functional groups are isocyanates, acid chlorides, and carboxylic acids from left to right. Where R can be, and is most certainly not limited to, any of the following chemical species (with any length aliphatic chain linker connecting the molecule to the functional group shown herein).

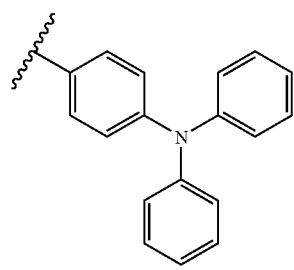

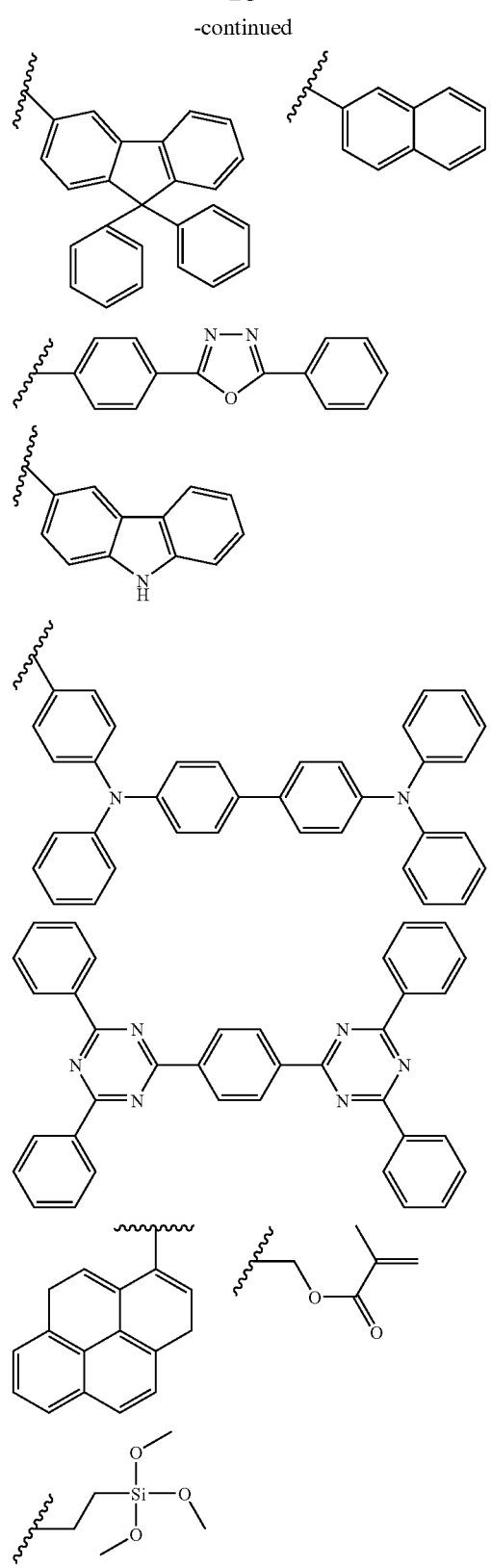

The system described herein can be further augmented by building similar variability into the phosphine oxide derivative used as the solvent in the overcoating procedure. This species has the formula:

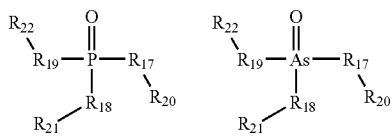

Wherein $R_{17}$, $R_{18}$, and $R_{19}$, which can be the same or different, represent a bond, an alkyl or alkylene group, an aryl or arylene group, a fluorocarbon group,

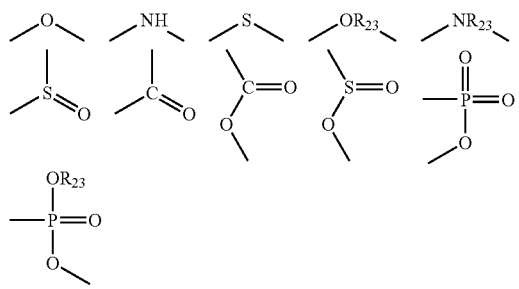

wherein $R_{23}$ is an alkyl or alkylene group or an aryl or arylene group; $R_{20}$, $R_{21}$, and $R_{22}$, which can be the same or different, represent hydrogen, an alkyl or alkylene group, an aryl or arylene group, —$OR_{24}$, —$NHR_{24}$, —$NR_{24}R_{24}$, —$SR_{24}$, wherein $R_{24}$ represents hydrogen, an alkyl group, or an aryl group.

To avoid the introduction of impurities which may have an unpredictable effect on the reaction, the ligands should preferably have a purity of at least 99 wt. %, and preferably greater than 99.5%.

Phosphinic or arsinic acid groups useful in the practice of the invention may include mono- and di-phosphinic/arsinic acid groups.

In accordance with certain embodiments of the present invention, a nanoparticle (e.g., a semiconductor nanocrystal) is formed, or overcoated in order to generate a shell on at least a portion of an outer surface of a nanoparticle, in the presence of molecules represented by one of the following formula or in the presence of molecules of both of the following formula:

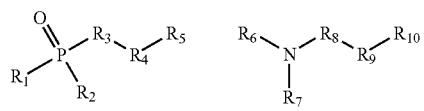

(in the above formula on the left, P can alternatively be As)

wherein $R_1$ represents a hydroxyl group; $R_2$ represents hydrogen, an alkyl or alkylene group, an aryl or arylene group, —$OR_{11}$, —$NHR_{11}$, —$NR_{11}R_{11}$, —$SR_{11}$, wherein $R_{11}$ represents hydrogen, an alkyl group, or an aryl group; $R_3$ and $R_4$, which can be the same or different, represent a bond, an alkyl or alkylene group, an aryl or arylene group, a fluorocarbon group,

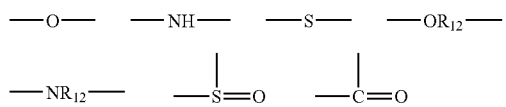

-continued

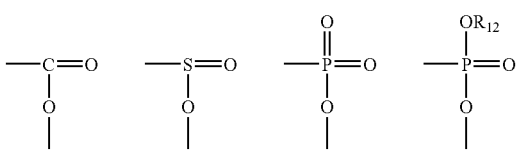

wherein $R_{12}$ is an alkyl or alkylene group or an aryl or arylene group; $R_5$ represents hydrogen, an alkyl group including one or more functional groups, an alkylene group, an aryl or arylene group, —$OR_{13}$, —$NHR_{13}$, —$NR_{13}R_{13}$, —$SR_{13}$, wherein $R_{13}$ represents hydrogen, an alkyl group, or an aryl group; $R_6$ represents hydrogen; $R_7$ represents hydrogen, an alkyl or alkylene group, an aryl or arylene group, —$OR_{14}$, —$NHR_{14}$, —$NR_{14}R_{14}$, —$SR_{14}$, wherein $R_{14}$ represents hydrogen, an alkyl group, or an aryl group; $R_8$ and $R_9$, which can be the same or different, represent a bond, an alkyl or alkylene group, an aryl or arylene group, a fluorocarbon group,

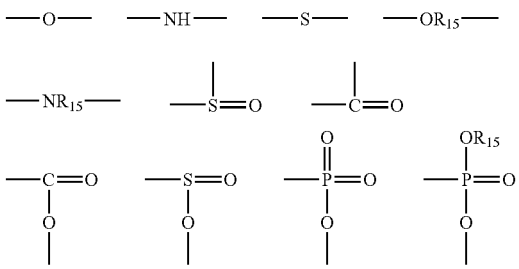

wherein $R_{15}$ is an alkyl or alkylene group or an aryl or arylene group; $R_{10}$ represents hydrogen, an alkyl group including one or more functional groups, an alkylene group, an aryl or arylene group, —$OR_{16}$, —$NHR_{16}$, —$NR_{16}R_{16}$, —$SR_{16}$, wherein $R_{16}$ represents hydrogen, an alkyl group, or an aryl group.

As mentioned herein, the system can be further augmented by building similar variability into the phosphine oxide derivative used as the solvent in the overcoating procedure. This species has the formula:

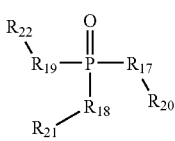

Wherein $R_{17}$, $R_{18}$, and $R_{19}$, which can be the same or different, represent a bond, an alkyl or alkylene group, an aryl or arylene group, a fluorocarbon group,

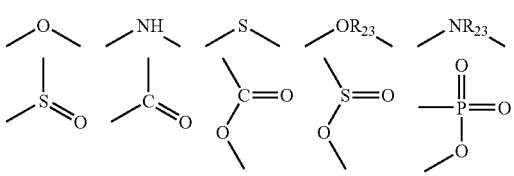

-continued

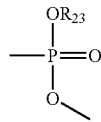

wherein $R_{23}$ is an alkyl or alkylene group or an aryl or arylene group; $R_{20}$, $R_{21}$, and $R_{22}$, which can be the same or different, represent hydrogen, an alkyl or alkylene group, an aryl or arylene group, —$OR_{24}$, —$NHR_{24}$, —$NR_{24}R_{24}$, —$SR_{24}$, wherein $R_{24}$ represents hydrogen, an alkyl group, or an aryl group.

To avoid the introduction of impurities which may have an unpredictable effect on the reaction, the ligands should preferably have a purity of at least 99 wt. %, and preferably greater than 99.5%.

Phosphinic acid groups useful in the practice of the invention may include mono and diphosphinic acid groups.

As described herein, arsenic variations of the above-described phosphorus-containing acid and oxide groups can also be used.

The present invention will be further clarified by the following examples, which are intended to be exemplary of the present invention.

EXAMPLES

Example 1A

Performing the overcoating procedure with TOPO as the solvent, replacing the existing aliphatic phosphonic acid and amine species with aromatic derivatives (see FIG. 1) results in semiconductor nanocrystals that have new surface chemistry while maintaining their optical properties. These semiconductor nanocrystals are no longer soluble in hexane, but are readily soluble in toluene and chloroform. In addition, thin films of organic molecules can be reliably deposited onto ordered films of these synthetically modified nanocrystals without the "puddling" associated with traditional aliphatic semiconductor nanocrystal surface chemistry (see FIGS. 2-5). It is believed that a phosphonic acid/amine salt is the predominant species on the surface of the semiconductor nanocrystal despite the fact that TOPO is in large excess during the reaction.

Preparation of Aromatic Semiconductor Nanocrystals Capable of Emitting Red Light Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Synthesis of CdSe/CdZnS Core-Shell Nanocrystals: 25.86 mmol of trioctylphosphine oxide and 2.4 mmol of benzylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure and then 2.4 mmol of phenylethylamine was added to the reaction mixture. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 ml, of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in toluene. The semiconductor nanocrystals had an emission maximum of 616 nm with a FWHM of 34 nm and a solution quantum yield of 50%.

Sample Fabrication. Cleaned glass substrates were ashed in a plasma preen and coated with PEDOT:PSS (70 nm). Substrates were taken into a nitrogen environment and baked at 120 C for 20 minutes. 50 nm E105 (N,N-Bis(3-methylphenyl)-N,N-bis-(phenyl)-9,9-spiro-bifluorene, LumTec) was evaporated in a vacuum chamber below 2e-6 Torr via thermal evaporation. Application of aromatic quantum dots was accomplished via contact printing. A dispersion of semiconductor nanocrystals with an optical density (OD) of 0.3 at the $1^{st}$ absorption feature was spin-coated at 3000 rpm on a parylene coated stamp for 60 seconds, which was then stamped onto the E105 substrates depositing a mono-layer of aromatic quantum dots. Substrates were then taken back into the thermal evaporation chamber, and 5 nm and 15 nm, respectively, of CBP (4,4'-Bis(carbazol-9-yl)biphenyl, LumTec) were evaporated below 2e-6 Torr. FIGS. 2-5 depict images of the samples described in this Sample Fabrication example.

Following examples 1-B and 1-C relate to preparing semiconductor nanocrystals including benzyl phosphonic acid ligands, but without the phenylethylamine shown in FIG. 1:

Example 1-B

Preparation of Semiconductor Nanocrystals Capable of Emitting Green Light

Synthesis of ZnSe Cores: 0.69 mmol diethyl zinc was dissolved in 5 ml, of tri-n-octylphosphine and mixed with 1 mL of 1 M TBP-Se, 28.9 mmol of Oleylamine was loaded into a 3-neck flask, dried and degassed at 90° C. for one hour. After degassing, the flask was heated to 310° C. under nitrogen. Once the temperature reached 310° C., the Zn solution was injected and the reaction mixture was heated at 270° C. for 15-30 minutes while aliquots of the solution were removed periodically in order to monitor the growth of the nanocrystals. Once the first absorption peak of the nanocrystals reached 350 nm, the reaction was stopped by dropping the flask temperature to 160° C. and used without further purification for preparation of CdZnSe cores.

Synthesis of CdZnSe Cores: 1.12 mmol dimethylcadmium was dissolved in 5 mL of tri-n-octylphosphine and mixed with 1 mL of 1 M TBP-Se. In a 4-neck flask, 41.38 mmol of trioctylphosphine oxide and 4 mmol of hexylphosphonic acid were loaded, dried and degassed at 120° C. for one hour. After degassing, the oxide/acid was heated to 160° C. under nitrogen and 8 ml of the ZnSe core growth solution was transferred at 160° C. into the flask, immediately followed by the addition of Cd/Se solution over the course of 20 minutes via syringe pump. The reaction mixture was then heated at 150° C. for 16-20 hours while aliquots of the solution were removed periodically in order to monitor the growth of the nanocrystals. Once the emission peak of the nanocrystals reached 500 nm, the reaction was stopped by cooling the mixture to room temperature. The CdZnSe cores were precipitated out of the growth solution inside a nitrogen atmosphere glovebox by adding a 2:1 mixture of methanol and n-butanol. The isolated cores were then dissolved in hexane and used to make core-shell materials.

Synthesis of CdZnSe/CdZnS Core-Shell Nanocrystals: 25.86 mmol of trioctylphosphine oxide and 2.4 mmol of benzylphosphonic acid were loaded into a four-neck flask. The mixture was then dried and degassed in the reaction vessel by heating to 120° C. for about an hour. The flask was then cooled to 75° C. and the hexane solution containing isolated CdZnSe cores (0.1 mmol Cd content) was added to the reaction mixture. The hexane was removed under reduced pressure. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 150° C. under nitrogen. The precursor solutions were added dropwise over the course of 1 hour at 150° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in hexane and used to make semiconductor nanocrystal composite materials, Example 1-C Preparation of Semiconductor Nanocrystals Capable of Emitting Red Light Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Synthesis of CdSe/CdZnS Core-Shell Nanocrystals: 25.86 mmol of trioctylphosphine oxide and 2.4 mmol of benzylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in toluene and used to make quantum dot composite materials.

Example 2

Figure 6:
FIG. 6 represents the chemical structures of examples of certain compositions useful in carrying out the present invention.

Performing the overcoating procedure with TOPO as the solvent, a fluorinated derivative of the amine species was used with hexylphosphonic acid, an aliphatic phosphonic acid (see FIG. 6). After the reaction, these semiconductor nanocrystals were no longer soluble in conventional organic solvents, such as hexane, toluene, chloroform, methylene chloride, etc. However, the sample was soluble in fluorinated solvents such as perfluorohexane, perfluorotoluene, and Fluorinert (FC-77). The level of fluorination could be enhanced by using the fluorinated amine with a fluorinated phosphonic acid derivative and/or a fluorinated TOPO equivalent in synthesis.

Fluorinating the surface of the semiconductor nanocrystals can facilitate deposition of the material in various applications. Fluorinated semiconductor nanocrystals have been successfully spin-cast directly onto organic thin-films since the fluorinated solvent was unable to solvate the organic transport materials.

Example 3

Figure 7:
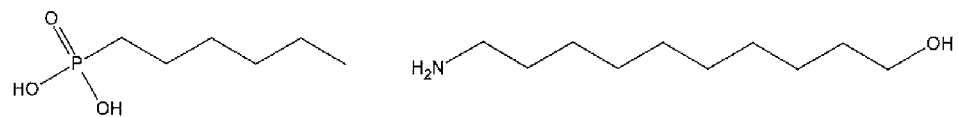
FIG. 7 represents the chemical structures of examples of certain compositions useful in carrying out the present invention.

Performing the overcoating procedure with TOPO as the solvent, an amine species functionalized with a terminal hydroxyl group was implemented with hexylphosphonic acid (see FIG. 7). After the reaction, the sample was not soluble in hexane or toluene but was soluble in polar solvents such as methanol and isopropanol. Again, polarity of the semiconductor nanocrystal surface could be enhanced by using an amine with an alkyl or aryl phosphonic acid with a terminal hydroxyl group and/or an alkyl or aryl phosphine oxide with a terminal hydroxyl group.

Example 4

Preparation of Semiconductor Nanocrystals Capable of Emitting Red Light

Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Synthesis of CdSe/CdZnS Core-Shell Nanocrystals: 25.86 mmol of trioctylphosphine oxide and 2.4 mmol of octadecylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure and then 2.4 mmol of 6-amino-1-hexanol was added to the reaction mixture. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in hexane.

Preparation of Layer including Semiconductor Nanocrystals

Films listed in Table 1 below are prepared using samples including semiconductor nanocrystals prepared substantially in accordance with one of the above-described examples dispersed in hexane. (A sample typically represents approximately 40 mg of solid dispersed in 10-15 ml hexane.) The hexane is removed from the semiconductor nanocrystals under vacuum at room temperature. Care is taken not to overdry or completely remove all solvent. 0.5 ml of RD-12, a low viscosity reactive diluent commercially available from Radcure Corp, 9 Audrey Pl, Fairfield, N.J. 07004-3401, United States, is added to the semiconductor nanocrystals while stirring magnetically. After the semiconductor nanocrystals are pre-solubilized in the reactive diluent, 2 ml of DR-150, UV-curable acrylic formulation commercially available Radcure, is added dropwise while stirring vigorously. Occasionally, the mixing vial is heated to lower viscosity and aid stirring. After the addition is competed, vacuum is pulled to remove entrained air. The vial is then placed in an ultrasonic bath (VWR) from 1 hour to overnight, resulting in a clear, colored solution. Care is taken to avoid temperatures over 40 C while the sample is in the ultrasonic bath.

Multiple batches of the semiconductor nanocrystals of the same color in UV curable acrylic are mixed together. For the samples below, the three red batches listed in Table 1 were added together; and four green batches listed in Table 1 were added together.

Samples are coated by Mayer rod on precleaned glass slides and cured in a 5000-EC UV Light Curing Flood Lamp from DYMAX Corporation system with an H-bulb (225 mW/cm$^2$) for 10 seconds.

Samples including multiple layers for achieving the desired thickness are cured between layers. Samples including filters on top of (or below) the semiconductor nanocrystal/matrix layers have the filters coated by Mayer rod in a separate step. Filters are made by blending UV-curable pigment ink formulations from Coates/Sun Chemical. A filter composition is formulated by adding the weighted absorbances of the individual colors together to achieve the desired transmission characteristics.

TABLE 1

| Film Color/Batch # (Nanocrystal Prep. Example #) | Solvent | Ligand(s) | Emission (nm) | FWHM | Solution QY (%) |
|---|---|---|---|---|---|
| Red/Batch #1 (Ex. 4) | Hexane | ODPA with 6-amino-1-hexanol | 617 | 40 | 73 |
| Red/Batch #2 (Ex. 4) | Hexane | ODPA with 6-amino-1-hexanol | 622 | 44 | 82 |
| Red/Batch #3 (Ex. 4) | Hexane | ODPA with 6-amino-1-hexanol | 624 | 44 | 73 |
| Green/Batch #1 (Ex 1A) | Hexane | Aromatic | 525 | 34 | 68 |
| Green/Batch #2 (Ex 1A) | Hexane | Aromatic | 527 | 34 | 66 |
| Green/Batch #3 (Ex 1A) | Hexane | Aromatic | 528 | 36 | 64 |
| Green/Batch #4 (Ex 1A) | Hexane | Aromatic | 530 | 33 | 60 |
| Green/Batch #5 (Ex 1A) | Hexane | Aromatic | 529 | 33 | 68 |

Examples of other variations for synthesizing semiconductor nanocrystals with aromatic surface functionality include the following. The overcoating process can be carried out in the absence of any ligand with an aliphatic group. In other words, the procedure can be performed without trioctylphosphine oxide (TOPO) or trioctylphosphine (TOP) and instead use a non-coordinating solvent (e.g., squalane). In order to maintain solubility of the semiconductor nanocrystals made in this process, multiple distinct aromatic phosphonic acid species and/or multiple distinct aromatic amine species may be included in the reaction in order to break-up crystallization or ordered packing of ligand species (both intra-semiconductor nanocrystal and inter-semiconductor nanocrystal) and allow the semiconductor nanocrystals to be dispersed in various solvent systems. Alternatively, branched phosphonic acids and/or branched amines can be used for this purpose.

Example 5

Preparation of Semiconductor Nanocrystals Capable of Emitting Red Light with 3,5-di-tert-butyl-4-hydroxybenzylphosphonic acid Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Preparation of 3,5-Di-tert-butyl-4-hydroxybenzylphosphonic acid 3,5-Di-tert-butyl-4-hydroxybenzylphosphonic acid was obtained from PCI Synthesis, 9 Opportunity Way, Newburyport, Mass. 01950.

The preparation of 3,5-Di-tert-butyl-4-hydroxybenzylphosphonic acid utilized the following synthetic approach:

3,5-Di-tert-butyl-4-hydroxybenzylphosphonic acid can be characterized by the following:
Melting point: 199-200° C. [Lit: 200° C.; Literature ref: J. D. Spivack, FR1555941 (1969)]
IR: 3614 cm$^{-1}$, 3593 cm$^{-1}$ (weak, O—H stretching).
$^1$H-NMR (CD$_3$OD): δ 7.10 (d, aromatic, 2H, J$_{P-H}$=2.6 Hz), 5.01 (s, exchanged HOD), 2.99 (d, —CH$_2$, 2H, J$_{P-H}$=21.2 Hz), 1.41 (s, —CH$_3$, 18H).
$^{13}$C-NMR (CD$_3$OD): δ 152.9 (aromatic), 137.9 (aromatic), 126.2 (aromatic), 123.5 (aromatic), 34.41 (d, —$\underline{C}$H$_2$, 35.75, 33.07, J$_{P-C}$=537.2 Hz), 34.35 (—$\underline{C}$(CH$_3$)$_3$), 29.7 (—C($\underline{C}$H$_3$)$_3$).
$^{31}$P-NMR (CD$_3$OD): δ 26.8

The above-identified synthetic precursors included in the preparation of 3,5-Di-tert-butyl-4-hydroxybenzylphosphonic acid can be characterized by the following:
Diethyl 3,5-di-tert-butyl-4-hydroxybenzylphosphonate
Melting point: 119-120° C. (Lit: 118-119° C.; Literature ref: R. K. Ismagilov, *Zhur. Obshchei Khimii*, 1991, 61, 387).
IR: 3451 cm$^-$ (weak, —OH, stretching), 2953 (weak, —CH$_3$, C—H stretching).
$^1$H-NMR (CDCl$_3$): δ 7.066 (d, Ar—H, 2H, J$_{P-H}$=2.8 Hz), 5.145 (s, 1H, —OH), 4.06-3.92 (m, —$\underline{C}$H$_2$CH$_3$, 4H, H—H and long-range P—H couplings), 3.057 (d, Ar—$\underline{C}$H$_2$, 2H, J$_{P-H}$=21.0 Hz), 1.412 (s, —C($\underline{C}$H$_3$)$_3$, 18H), 1.222 (t, —CH$_2$C$\underline{H}$$_3$, 6H).
$^H$C-NMR (CDCl$_3$): δ 153.98 (aromatic), 136.22 (aromatic), 126.61 (aromatic), 122.07 (aromatic), 62.14 (—O$\underline{C}$H$_2$CH$_3$, J$_{P-C}$=24.4 Hz), 33.63 (Ar—$\underline{C}$H$_2$, J$_{P-C}$=552.4 Hz), 34.53 [—$\underline{C}$(CH$_3$)$_3$], 30.54 [['C($\underline{C}$H$_3$)$_3$], 16.66 (—CH$_2$$\underline{C}$H$_3$, J$_{P-C}$=24.4 Hz).
$^{31}$P-NMR (CDCl$_3$): δ 28.43.
3,5-di-tert-butyl-4-hydroxybenzyl bromide
Melting point: 51-54° C. (Lit: 52-54° C.; Literature ref: J. D. McClure, *J. Org. Chem.*, 1962, 27, 2365)
IR: 3616 cm$^{-1}$ (medium, O—H stretching), 2954 cm$^{-1}$ (weak, alkyl C—H stretching).

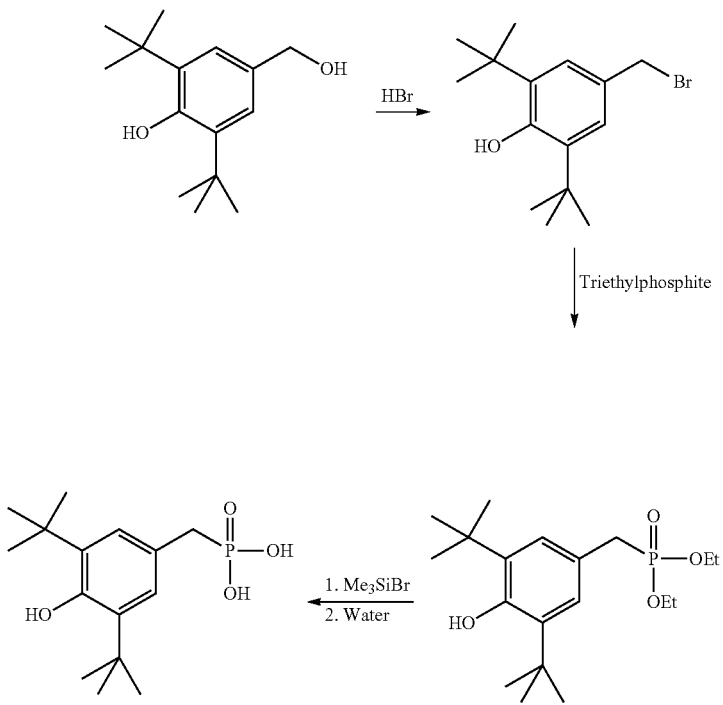

$^1$H-NMR (CDCl$_3$): δ 7.20 (s, Ar—H, 2H), 5.31 (s, —OH), 4.51 (s, —CH$_2$, 2H), 1.44 {s, [—C(CH$_3$)$_3$], 18H}.

$^{13}$C-NMR (CDCl$_3$): δ 154.3 (aromatic), 136.5 (aromatic), 128.7 (aromatic), 126.3 (aromatic), 35.8 [(—C(CH$_3$)$_3$], 34.6 (—CH$_2$), 30.5 [—C(CH$_3$)$_3$].

Other synthetic approaches that are known or readily ascertainable by one of ordinary skill in the relevant art can be used to prepare 3,5-Di-tert-butyl-4-hydroxybenzylphosphonic acid.

Synthesis of CdSe/CdZnS Core-Shell Nanocrystals:

25.86 mmol of trioctylphosphine oxide and 2.4 mmol of 3,5-di-tert-butyl-4-hydroxybenzylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in chloroform and used to make semiconductor nanocrystal composite materials.

In Table 2, the 3,5-di-tert-butyl-4-hydroxybenzylphosphonic acid ligand group is referred to as BHT.

Preparation of Layer Including Semiconductor Nanocrystals

Films listed in Table 2 below are prepared using samples including semiconductor nanocrystals prepared substantially in accordance with the synthesis described in Example 5. Bulk chloroform is removed from the nanocrystal samples with nitrogen purging. Residual chloroform is removed from the semiconductor nanocrystals under vacuum at room temperature. Care is taken not to overdry or completely remove all solvent.

37 ml of RD-12, a low viscosity reactive diluent commercially available from Radcure Corp, 9 Audrey Pl, Fairfield, N.J. 07004-3401. United States, is added to 4.68 gram of semiconductor nanocrystals under vacuum. The vessel is then backfilled with nitrogen and the mixture is mixed using a vortex mixer. After the semiconductor nanocrystals are pre-solubilized in the reactive diluent, 156 ml of DR-150, an UV-curable acrylic formulation commercially available Radcure, is added slowly under vacuum. The vessel is then backfilled with nitrogen and the mixture is mixed using a vortex mixer.

2.00 gram TiO2 (if indicated) is next added and the mixture is mixed with an homogenizer.

12.00 gram curing agent Escacure TPO is added, following which the mixture is mixed with an homogenizer. The vessel including the mixture is then wrapped with black tape to shield the fluid from light.

The vessel in then backfilled with nitrogen and sonified for at least about 3 hours. Care is taken to avoid temperatures over 40 C while the sample is in the ultrasonic bath.

Samples are coated by Mayer rod on precleaned glass slides and cured in a 5000-EC UV Light Curing Flood Lamp from DYMAX Corporation system with an H-bulb (225 mW/cm$^2$) for 10 seconds.

A sample is removed for evaluation and coated on a glass slide with a 52 rod and cured for 10 sec:

| Thickness = 72 μm | |
| Lambda em = 633.1 nm | FWHM = 36 nm |
| % EQE = 50.0% | % A$_{450\,nm}$ = 82.6% |

Occasionally, the mixing vial is heated to lower viscosity and aid stirring. After the addition is competed, vacuum is pulled to remove entrained air. The vial is then placed in an ultrasonic bath (VWR) from 1 hour to overnight, resulting in a clear, colored solution. Care is taken to avoid temperatures over 40 C while the sample is in the ultrasonic bath.

Multiple batches of the semiconductor nanocrystals of the same color are mixed together. Prior to making the acrylic preparation. Samples are coated by Mayer rod on precleaned glass slides and cured in a 5000-EC UV Light Curing Flood Lamp from DYMAX Corporation system with an H-bulb (225 mW/cm$^2$) for 10 seconds.

Samples including multiple layers for achieving the desired thickness are cured between layers. Samples including filters on top of (or below) the layers including host material and quantum confined semiconductor nanoparticles have the filters coated by Mayer rod in a separate step.

Filters are made by blending UV-curable pigment ink formulations from Coates/Sun Chemical. (Examples include, but are not limited to, DXT-1935 and WIN99.) A filter composition is formulated by adding the weighted absorbances of the individual colors together to achieve the desired transmission characteristics.

TABLE 2

| Film Color/Sample # (Nanocrystal Prep. Example #) | Solvent | Ligand(s) | Emission (nm) | FWHM | Film EQE (%) |
|---|---|---|---|---|---|
| Red/Sample #1 (without TiO2) (Ex. 5) | Chloroform | BHT | 631 | 36 | 29.0 |
| Red/Sample #2 (with TiO2) (Ex. 5) | Chloroform | BHT | 633 | 36 | 50.0 |

Figure 8:
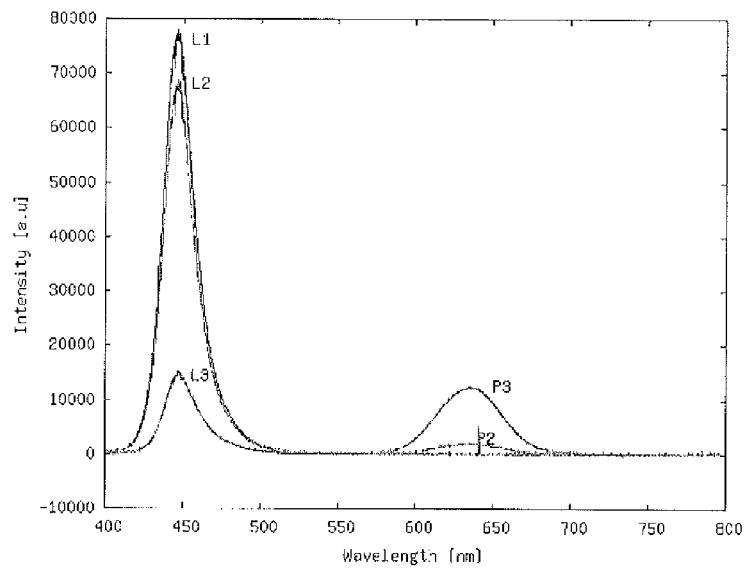
FIG. 8 depicts spectra to illustrate a method for measuring quantum efficiency.

Film Characterization:
 The films are characterized in the following ways:
 Thickness: measured by a micrometer
 Emission measurement measured on sample 1 of each type, on Cary Eclipse. Excitation at 450 nm, 2.5 nm excitation slit, 5 nm emission slit.
 Absorption measured at 450 nm on sample 1 of each type, on Cary 5000. Baseline corrected to blank glass slide.
 CIE coordinates measured on sample 1 of each type using CS-200 Chroma Meter. Sample excited with 450 nm LED, and camera collected color data off axis.
 The external photoluminescent (PL) quantum efficiency is measured using the method developed by Mello et al. (1). The method uses a collimated 450 nm LED source, an integrating sphere and a spectrometer. Three measurements are taken. First, the LED directly illuminates the integrating sphere giving the spectrum labeled L1 in FIG. 8. Next, the PL sample is placed into the integrating sphere so that only diffuse LED light illuminates the sample giving the (L2+P2) spectrum depicted in FIG. 8. Finally, the PL sample is placed into the integrating sphere so that the LED directly illuminates the sample (just off normal incidence) giving the (L3+P3) spectrum depicted in FIG. 8. After collecting the data, each spectral contribution (L's and P's) is computed. L1, L2 and L3 correspond to the sums of the LED spectra for each measurement and P2 and P3 are the sums associated with the PL spectra for 2nd and 3rd measurements. The following equation then gives the external PL quantum efficiency:

$$EQE = [(P3 \cdot L2) \text{minus} (P2 \cdot L3)] / (L1 \cdot (L2 \text{minus} L3))$$

For additional information concerning EQE measurements, see Mello et al., Advanced Materials 9(3):230 (1997), which is hereby incorporated by reference.

In certain embodiments, semiconductor nanocrystals are purified before deposition.

In certain embodiments, a desired ligand can be attached to a semiconductor nanocrystal by building the desired functionality into the phosphonic acid derivative, amine derivative, or both. Following is a non-limiting example of a schematic of a general synthetic procedure for generating a desired phosphonic acid derivative:

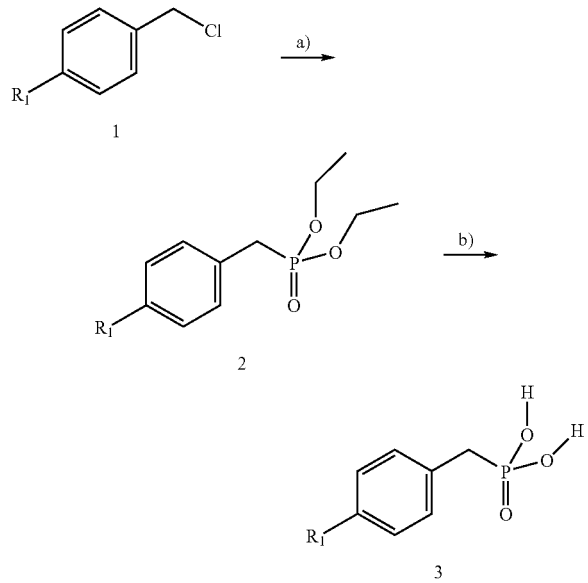

a) NaH, THF, NaI and 1.
b) 1. TMSBr, CH$_2$Cl$_2$, 2. H$_2$O.

Also refer to *The Chemistry of Organophosphorus Compounds, Volume* 4: *Ter-and Quinque-Valent Phosphorus Acids and Their Derivatives*, Frank R. Hartley (Editor), April 1996 for more general synthetic procedures for generating phosphonic acid derivatives.

In certain additional embodiments, a desired ligand can be attached to a semiconductor nanocrystal by building the desired functionality into the phosphonic acid derivative, amine derivative, or both. Following is a non-limiting example of a schematic of a general synthetic procedure for generating a desired amine derivative:

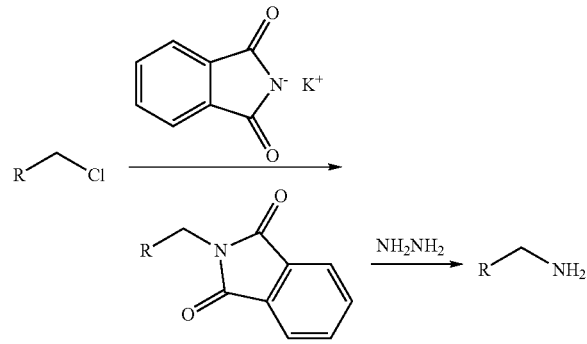

Example 6

Comparison of Semiconductor Nanocrystals Prepared with Native Ligands & Semiconductor Nanocrystals with Cap Exchanged Ligands Example 6A Preparation of Semiconductor Nanocrystals Capable of Emitting Red Light Including Native Ligands Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioetylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Synthesis of CdSe/CdZnS Core-Shell Nanocrystals: 25.86 mmol of trioctylphosphine oxide and 2.4 mmol of octadecylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure and then 2.4 mmol of 6-amino-1-hexanol was added to the reaction mixture. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C.

using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in hexane and their solution-state quantum yield assessed. (QY~80%)

Example 6B

Preparation of Cap Exchanged Semiconductor Nanocrystals Capable of Emitting Red Light Synthesis of CdSe Cores: 1 mmol cadmium acetate was dissolved in 8.96 mmol of tri-n-octylphosphine at 100° C. in a 20 mL vial and then dried and degassed for one hour. 15.5 mmol of trioctylphosphine oxide and 2 mmol of octadecylphosphonic acid were added to a 3-neck flask and dried and degassed at 140° C. for one hour. After degassing, the Cd solution was added to the oxide/acid flask and the mixture was heated to 270° C. under nitrogen. Once the temperature reached 270° C., 8 mmol of tri-n-butylphosphine was injected into the flask. The temperature was brought back to 270° C. where 1.1 mL of 1.5 M TBP-Se was then rapidly injected. The reaction mixture was heated at 270° C. for 15-30 minutes while aliquots of the solution were removed periodically in order to monitor the growth of the nanocrystals. Once the first absorption peak of the nanocrystals reached 565-575 nm, the reaction was stopped by cooling the mixture to room temperature. The CdSe cores were precipitated out of the growth solution inside a nitrogen atmosphere glovebox by adding a 3:1 mixture of methanol and isopropanol. The isolated cores were then dissolved in hexane and used to make core-shell materials.

Synthesis of CdSe/CdZnS Core-Shell Nanocrystals: 25.86 mmol of trioctylphosphine oxide and 2.4 mmol of octadecylphosphonic acid were loaded into a four-neck flask. The mixture was then dried and degassed in the reaction vessel by heating to 120° C. for about an hour. The flask was then cooled to 75° C. and the hexane solution containing isolated CdSe cores (0.1 mmol Cd content) was added to the reaction mixture. The hexane was removed under reduced pressure and then 2.4 mmol of decylamine was added to the reaction mixture. Dimethyl cadmium, diethyl zinc, and hexamethyldisilathiane were used as the Cd, Zn, and S precursors, respectively. The Cd and Zn were mixed in equimolar ratios while the S was in two-fold excess relative to the Cd and Zn. The Cd/Zn and S samples were each dissolved in 4 mL of trioctylphosphine inside a nitrogen atmosphere glove box. Once the precursor solutions were prepared, the reaction flask was heated to 155° C. under nitrogen. The precursor solutions were added dropwise over the course of 2 hours at 155° C. using a syringe pump. After the shell growth, the nanocrystals were transferred to a nitrogen atmosphere glovebox and precipitated out of the growth solution by adding a 3:1 mixture of methanol and isopropanol. The isolated core-shell nanocrystals were then dissolved in hexane and used for cap exchange reactions. (QY~80%)

Cap-exchange reaction (1) on CdSe/CdZnS Core-Shell Nanocrystals: 10 mL of toluene and 42.6 mmol of 6-amino-1-hexanol were loaded into a four-neck flask. The flask was evacuated and refilled with nitrogen three times. The flask was then heated to 40° C. and the hexane solution containing isolated CdSe/CdZnS core/shell (1 prep) was added to the reaction mixture. The mixture was heated at 40° C. overnight. Finally, the cap-exchanged semiconductor nanocrystals were precipitated out of the growth solution by adding hexane. The isolated core-shell nanocrystals were then dissolved in a 3:1 methanol and isopropanol mixture and their solution-state quantum yield assessed. (QY~15%)

Cap-exchange reaction (2) on CdSe/CdZnS Core-Shell Nanocrystals: 25.86 mmol of trioctylphosphine oxide, 2.4 mmol of octadecylphosphonic acid, and 2.4 mmol of 6-amino-1-hexanol were loaded into a four-neck flask. The mixture was then dried and degassed in the reaction vessel by heating to 120° C. for about an hour. The flask was then cooled to 40° C. and the hexane solution containing isolated CdSe/CdZnS core/shell (1 prep) was added to the reaction mixture. The mixture was heated at 40° C. overnight. Finally, the cap-exchanged semiconductor nanocrystals were precipitated out of the growth solution by adding a 3:1 mixture of methanol and isopropanol. The isolated core-shell nanocrystals were then dissolved in hexane and their solution-state quantum yield assessed. (QY~19%)

Nanoparticles can have various shapes, including, but not limited to, sphere, rod, disk, other shapes, and mixtures of various shaped particles.

Metallic nanoparticles can be prepared as described, for example, in U.S. Pat. No. 6,054,495, which is incorporated by reference in its entirety. The metallic nanoparticle can be a noble metal nanoparticle, such as a gold nanoparticle. Gold nanoparticles can be prepared as described in U.S. Pat. No. 6,506,564, which is incorporated by reference in its entirety. Ceramic nanoparticles can be prepared as described, for example, in U.S. Pat. No. 6,139,585, which is incorporated by reference in its entirety.

Narrow size distribution, high quality semiconductor nanocrystals with high fluorescence efficiency can be prepared using previously established literature procedures and used as the building blocks. See, C. B. Murray et al., *J. Amer. Chem. Soc.* 1993, 115, 8706, B. O. Dabbousi et al., *J. Phys. Chem. B* 1997, 101, 9463, each of which is incorporated by reference in its entirety. Other methods known or readily ascertainable by the skilled artisan can also be used.

In certain embodiments, nanoparticles comprise chemically synthesized colloidal nanoparticles (nanoparticles), such as semiconductor nanocrystals or quantum dots. In certain preferred embodiments, the nanoparticles (e.g., semiconductor nanocrystals) have a diameter in a range from about 1 to about 10 nm. In certain embodiments, at least a portion of the nanoparticles, and preferably all of the nanoparticles, include one or more ligands attached to a surface of a nanoparticle. See, C. B. Murray et al., *Anna. Rev. Mat. Sci.,* 30, 545-610 (2000), which is incorporated in its entirety. These zero-dimensional structures show strong quantum confinement effects that can be harnessed in designing bottom-up chemical approaches to create complex heterostructures with electronic and optical properties that are tunable with the size of the nanocrystals.

Emission from semiconductor nanocrystals can occur at an emission wavelength when one or more of the nanociystals is excited. The emission has a frequency that corresponds to the band gap of the quantum confined semiconductor material. The band gap is a function of the size of the nanocrystal. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases.

The emission from a nanocrystal can be a narrow Gaussian emission band that can be tuned through the complete wavelength range of the ultraviolet, visible, or infrared regions of the spectrum by varying the size of the nanocrystal, the composition of the nanocrystal, or both. The narrow size distribution of a population of nanocrystals can result in emission of light in a narrow spectral range. The population can be monodisperse and can exhibit less than a 15% rms deviation in diameter of the nanocrystals, preferably less than 10%, more preferably less than 5%. Spectral emissions in a narrow range of no greater than about 75 nm, preferably 60 nm, more preferably 40 nm, and most preferably 30 nm full width at half max (FWHM) can be observed. The breadth of the emission decreases as the dispersity of nanocrystal diameters decreases.

Semiconductor nanocrystals can have high emission quantum efficiencies such as greater than 10%, 20%, 30%, 40%, 50%, 60%, 70%, or 80%, The semiconductor forming the nanocrystals can include Group IV elements, Group II-VI compounds, Group II-V compounds, Group III-VI compounds, Group III-V compounds, Group IV-VI compounds, Group I-III-VI compounds, Group II-IV-VI compounds, or Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

Examples of methods of preparing monodisperse semiconductor nanocrystals include pyrolysis of organometallic reagents, such as dimethyl cadmium, injected into a hot, coordinating solvent. This permits discrete nucleation and results in the controlled growth of macroscopic quantities of nanocrystals. Preparation and manipulation of nanocrystals are described, for example, in U.S. Pat. No. 6,322,901, which is incorporated herein by reference in its entirety. Such methods of manufacturing nanocrystals involve a colloidal growth process. Colloidal growth occurs by rapidly injecting an M donor and an X donor into a hot coordinating solvent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating solvent that follows nucleation can also result in uniform surface derivatization and regular core structures. As the size distribution sharpens, the temperature can be raised to maintain steady growth. By adding more M donor or X donor, the growth period can be shortened.

The M donor can be an inorganic compound, an organometallic compound, or elemental metal. For example, M can be cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis(silyl)chalcogenide, dioxygen, an ammonium salt, or a tris(silyl)pnictide. Suitable X donors include dioxygen, bis(trimethylsilyl)selenide ((TMS)$_2$Se), trialkyl phosphine selenides such as (tri-n-octylphosphine)selenide (TOPSe) or (tri-n-butylphosphine)selenide (TBPSe), trialkyl phosphine tellurides such as (tri-n-octylphosphine)telluride (TOPTe) or hexapropylphosphorustriamide telluride (HPPTTe), bis(trimethylsilyl)telluride ((TMS)$_2$Te), bis(trimethylsilyl)sulfide ((TMS)$_2$S), a trialkyl phosphine sulfide such as (tri-n-octylphosphine)sulfide (TOPS), an ammonium salt such as an ammonium halide (e.g., NH$_4$Cl), tris(trimethylsilyl)phosphide ((TMS)$_3$P), tris(trimethylsilyl)arsenide ((TMS)$_3$As), or tris(trimethylsilyl)antimonide ((TMS)$_3$Sb). In certain embodiments, the M donor and the X donor can be moieties within the same molecule.

A coordinating solvent can help control the growth of nanocrystals. The coordinating solvent is a compound having a donor lone pair that, for example, has a lone electron pair available to coordinate to a surface of the growing nanocrystal. Solvent coordination can stabilize the growing nanocrystal. Typical coordinating solvents include alkyl phosphines, alkyl phosphine oxides, alkyl phosphoric acids, or alkyl phosphinic acids, however, other coordinating solvents, such as pyridines, furans, and amines may also be suitable for the nanocrystal production. Examples of suitable coordinating solvents include pyridine, tri-n-octyl phosphine (TOP), tri-n-octyl phosphine oxide (TOPO) and tris-hydroxylpropylphosphine (tHPP). Technical grade TOPO can be used.

In certain methods, a non-coordinating or weakly coordinating solvent can be used.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter and choosing the proper composition of the semiconducting material, the emission spectra of the nanocrystals can be tuned continuously over the wavelength range of 300 nm to 5 microns.

Semiconductor nanocrystals include, for example, inorganic crystallites between about 1 nm and about 1000 nm in diameter, preferably between about 2 nm and about 50 um, more preferably about 1 nm to about 20 nm (such as about 6, 7, 8, 9, 10, 11, 12, 13, 14, 15, 16, 17, 18, 19, or 20 nm).

A semiconductor nanocrystal typically has a diameter of less than 150 Å. A population of nanocrystals preferably has average diameters in the range of 15 Å to 125 Å.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M comprises one or more metals (e.g., but not limited to, cadmium, zinc, magnesium, mercury, aluminum, gallium, indium, thallium, or mixtures thereof), and X comprises one or more members of Group IV, V, or VI (e.g., but not limited to, oxygen, sulfur, selenium, tellurium, nitrogen, phosphorus, arsenic, antimony, or mixtures thereof). In certain embodiments, a nanocrystal can comprise a Group II-VI compound, Group II-V compound, Group III-VI compound, Group III-V compound, Group IV-VI compound, Group I-III-VI compound, Group II-IV-VI compound, and Group II-IV-V compound. In certain embodiments, a nanocrystal can comprise a Group IV element.

The core can have an overcoating on a surface of the core. The overcoating can be a semiconductor material having a composition different from the composition of the core. The overcoat of a semiconductor material on a surface of the nanocrystal can include a Group II-VI compound, Group II-V compound, Group III-VI compound, Group III-V compound, Group IV-VI compound, Group I-III-VI compound, Group II-IV-VI compound, and Group II-IV-V compound, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. In certain embodiments, a nanocrystal can comprise a Group IV element.

For example, ZnS, ZnSe or CdS overcoatings can be grown on CdSe or CdTe nanocrystals. An overcoating process is described, for example, in U.S. Pat. No. 6,322,901. By adjusting the temperature of the reaction mixture during overcoating and monitoring the absorption spectrum of the core, over coated materials having high emission quantum efficiencies and narrow size distributions can be obtained.

The particle size distribution can be further refined by size selective precipitation with a poor solvent for the nanocrystals, such as methanol/butanol as described in U.S. Pat. No. 6,322,901. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

Transmission electron microscopy (TEM) can provide information about the size, shape, and distribution of the nanocrystal population. Powder x-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from x-ray diffraction data using, for example, the Schemer equation. It also can be estimated from the UV/Vis absorption spectrum.

Narrow FWHM of nanocrystals can result in saturated color emission. This can lead to efficient nanocrystal-light emitting devices even in the red and blue parts of the spectrum, since in nanocrystal emitting devices no photons are lost to infrared and UV emission. The broadly tunable, saturated color emission over the entire visible spectrum of a single material system is unmatched by any class of organic chromophores. Furthermore, environmental stability of covalently bonded inorganic nanocrystals suggests that device lifetimes of hybrid organic/inorganic light emitting devices should match or exceed that of all-organic light emitting devices, when nanocrystals are used as luminescent centers. The degeneracy of the band edge energy levels of nanocrystals facilitates capture and radiative recombination of all possible excitons, whether generated by direct charge injection or energy transfer. The maximum theoretical nanocrystal-light emitting device efficiencies are therefore comparable to the unity efficiency of phosphorescent organic light emitting devices. The nanocrystal's excited state lifetime ($\tau$) is much shorter ($\tau \approx 10$ ns) than a typical phosphor ($\tau > 0.5$ $\mu$s), enabling nanocrystal-light emitting devices to operate efficiently even at high current density.

Semiconductor nanocrystals in accordance with the present inventions can be included in emissive materials for use in light-emitting devices, displays, and other optoelectronic and electronic devices, including, but not limited to, those described, for example, in International Application No. PCT/US2007/013152, entitled "Light-Emitting Devices And Displays With Improved Performance", of QD Vision, Inc. et al., filed 4 Jun. 2007, which is hereby incorporated herein by reference in its entirety.

Semiconductor nanocrystals in accordance with the present inventions can be included in photoluminescent applications including, but not limited to, those described in U.S. Application No. 60/971885, of Coe-Sullivan, et al., entitled "Optical Component, System Including An Optical Component, Devices, And Composition", filed 12 Sep. 2007, and U.S. Application No. 60/973644, entitled "Optical Component, System Including An Optical Component, Devices, And Composition", of Coe-Sullivan, et al, filed 19 Sep. 2007, each of which is hereby incorporated herein by reference in its entirety.

Other materials, techniques, methods, applications, and information that may be useful with the present invention are described in International Patent Application No. PCT/US2007/24750, entitled "Improved Composites And Devices Including Nanoparticles", of Coe-Sullivan, et al, filed 3 Dec. 2007, and U.S. Application No. 60/971887, entitled "Functionalized Semiconductor Nanocrystals And Method", of Breen, et al., filed 12 Sep. 2007; and International Application No. PCT/US2007/014711, entitled "Methods For Depositing Nanomaterial, Methods For Fabricating A Device, And Methods For Fabricating An Array Of Devices", of QD Vision, Inc. et al., filed 25 Jun. 2007; each of the foregoing being hereby incorporated herein by reference in its entirety.

As used herein, the singular forms "a", "an" and "the" include plural unless the context clearly dictates otherwise. Thus, for example, reference to an emissive material includes reference to one or more of such materials.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. Additional embodiments of the present invention will also be apparent to those skilled in the art from consideration of the specification and practice of the invention disclosed herein. It is intended that the specification and examples be considered as exemplary only, with a true scope and spirit of the invention being indicated by the following claims and equivalents thereof.

All patents, patent applications, and publications mentioned above are herein incorporated by reference in their entirety for all purposes. None of the patents, patent applications, and publications mentioned herein are admitted to be prior art.

What is claimed is:

1. A nanoparticle comprising a semiconductor nanocrystal capable of emitting light, the nanoparticle including one or more chemically distinct native ligands attached to a surface thereof, at least one of said ligands being represented by the formula:

X-Sp-Z wherein X represents a phosphonic acid group; Sp represents a spacer group comprising a group capable of allowing a transfer of charge or an insulating group; and Z represents: (i) a reactive group capable of communicating specific chemical properties to the nanoparticle as well as provide specific chemical reactivity to the surface of the nanoparticle, and/or (ii) a group that is cyclic, halogenated, and/or polar a-protic, wherein Z in all cases is not reactive upon exposure to light, and wherein a native ligand is a ligand that attaches or coordinates to the nanoparticle surface during the growth thereof or overcoating thereof with an overcoating material comprising a semiconductor material.

2. A nanoparticle in accordance with claim 1 wherein Z does not render the nanoparticle dispersible in a liquid medium that includes water.

3. A nanoparticle in accordance with claim 1 wherein the reactive group comprises a functional, bifunctional, or polyfunctional reagent, and/or a reactive chemical group.

4. A nanoparticle in accordance with claim 1 wherein the cyclic group comprises a saturated or unsaturated cyclic or bicyclic compound or aromatic compound.

5. A nanoparticle in accordance with claim 1 wherein the cyclic group includes at least one hetero-atom and/or at least one substituent group.

6. A nanoparticle in accordance with claim 1 wherein the halogenated group comprises a fluorinated group, perfluorinated group, a chlorinated group, a perchlorinated group, a brominated group, a perbrominated group, an iodinated group, a periodinated group.

7. A nanoparticle in accordance with claim 1 wherein the polar a-protic group comprises a ketone, aldehyde, amide, urea, urethane, or an imine.

8. A nanoparticle in accordance with claim 1 wherein the semiconductor nanocrystal comprises a core comprising a first material and a shell disposed over at least a portion of a surface of the core, the shell comprising a second material.

9. A nanoparticle in accordance with claim 8 wherein the first material comprises a semiconductor material.

10. A nanoparticle in accordance with claim 8 wherein the second material comprises a semiconductor material.

11. A nanoparticle in accordance with claim 8 wherein one or more additional shells are disposed over at least a portion of a surface of the shell.

12. A nanoparticle in accordance with claim 1 wherein the ligand represented by the formula X-Sp-Z comprises benzylphosphonic acid, benzylphosphonic acid including at least one substituent group on the ring of the benzyl group, a conjugate base of one of benzylphosphonic acid and benzylphosphonic acid including at least one substituent group on the ring of the benzyl group, or a mixture including one or more of benzylphosphonic acid, benzylphosphonic acid including at least one substituent group on the ring of the benzyl group, a conjugate base of benzylphosphonic acid, and conjugate base of benzylphosphonic acid including at least one substituent group on the ring of the benzyl group.

13. A nanoparticle comprising a semiconductor nanocrystal capable of emitting light, the nanoparticle including one or more chemically distinct native ligands attached to a surface thereof, at least one of said ligands being represented by the formula:

X-Sp-Z wherein X represents a primary amine group, a secondary amine group, a urea, a thiourea, an amide group, a phosphonic or arsonic acid group, a phosphinic or arsinic acid group, an arsenate group, a phosphine or arsine oxide group; Sp represents a spacer group comprising a group capable of allowing a transfer of charge or an insulating group; and Z represents: (i) a reactive group capable of communicating specific chemical properties to the nanoparticle as well as provide specific chemical reactivity to the surface of the nanoparticle, and/or (ii) a group that is cyclic, halogenated, and/or polar a-protic, wherein Z in all cases is not reactive upon exposure to light, wherein the ligand represented by the formula X-Sp-Z comprises 3, 5-di-tert-butyl-4-hydroxybenzylphosphonic acid, a conjugate base of the acid, or a mixture including one or more of 3, 5-di-tert-butyl-4-hydroxybenzylphosphonic acid and the conjugate base of the acid.

14. A nanoparticle in accordance with claim 1 wherein the nanoparticle includes two or more chemically distinct native ligands attached to a surface thereof, at least one of said ligands being represented by the formula:

X-Sp-Z.

15. A nanoparticle in accordance with claim 1 including two or more chemically distinct native ligands attached to a surface thereof, wherein a first ligand is represented by the formula:

N-Sp-Z wherein N represents a primary amine group, a secondary amine group, an amide group; and
a second ligand is represented by the formula:

X-Sp-Z wherein X represents a phosphonic acid group; and
wherein Sp represents a spacer group comprising a group capable of allowing a transfer of charge or an insulating group; and Z represents: (i) a reactive group capable of communicating specific chemical properties to the nanoparticle as well as provide specific chemical reactivity to the surface of the nanoparticle, and/or (ii) a group that is cyclic, halogenated, and/or polar a-protic, wherein Z in all cases is not reactive upon exposure to light, and wherein a native ligand is a ligand that attaches or coordinates to the nanoparticle surface during the growth thereof or overcoating thereof with an overcoating material comprising a semiconductor material, and each of Sp and Z on the first ligand and on the second ligand can be the same or different.

16. A nanoparticle in accordance with claim 1 wherein the nanoparticle has higher quantum yield than if the same ligand was attached to the nanoparticle by a ligand exchange process.

17. A nanoparticle in accordance with claim 14 wherein the ligand represented by the formula X-Sp-Z comprises benzylphosphonic acid, benzylphosphonic acid including at least one substituent group on the ring of the benzyl group, a conjugate base of one of benzylphosphonic acid and benzylphosphonic acid including at least one substituent group on the ring of the benzyl group, or a mixture including one or more of benzylphosphonic acid, benzylphosphonic acid including at least one substituent group on the ring of the benzyl group, a conjugate base of benzylphosphonic acid, and conjugate base of benzylphosphonic acid including at least one substituent group on the ring of the benzyl group.

18. A nanoparticle comprising a semiconductor nanocrystal capable of emitting light, the nanoparticle including two or more chemically distinct native ligands attached to a surface thereof, at least one of said ligands being represented by the formula:

X-Sp-Z wherein X represents a primary amine group, a secondary amine group, a urea, a thiourea, an amide group, a phosphonic or arsonic acid group, a phosphinic or arsinic acid group, an arsenate group, a phosphine or arsine oxide group; Sp represents a spacer group comprising a group capable of allowing a transfer of charge or an insulating group; and Z represents: (i) a reactive group capable of communicating specific chemical properties to the nanoparticle as well as provide specific chemical reactivity to the surface of the nanoparticle, and/or (ii) a group that is cyclic, halogenated, and/or polar a-protic, wherein Z in all cases is not reactive upon exposure to light, wherein the ligand represented by the formula X-Sp-Z comprises 3, 5-di-tert-butyl-4-hydroxybenzylphosphonic acid, a conjugate base of the acid, or a mixture including one or more of 3, 5-di-tert-butyl-4-hydroxybenzylphosphonic acid and the conjugate base of the acid.

19. A nanoparticle in accordance with claim 1 wherein Sp comprises a straight or branched $C_1$-$C_{18}$ hydrocarbon chain.

20. A nanoparticle in accordance with claim 19 wherein the hydrocarbon chain includes at least one double bond, at least one triple bond, or at least one double bond and one triple bond.

21. A nanoparticle in accordance with claim 19 wherein the hydrocarbon chain is interrupted by —O—, —S—, —N($R_a$)—, —N($R_a$)—C(O)—O—, —O—C(O)—N($R_a$)—, —N($R_a$)—C(O)—N($R_b$)—, —O—C(O)—O—, —P(Ra)—, or —P(O)($R_a$)—, wherein each of $R_a$ and $R_b$, independently, is hydrogen, alkyl, alkenyl, alkynyl, alkoxy, hydroxylalkyl, hydroxyl, or haloalkyl.

22. A nanoparticle in accordance with claim 12 wherein the semiconductor nanocrystal comprises a core comprising a first material and a shell disposed over at least a portion of a surface of the core, the shell comprising a second material.

23. A nanoparticle in accordance with claim 22 further including one or more additional shells disposed over at least a portion of the shell.

* * * * *